(12) United States Patent
Stratton et al.

(10) Patent No.: US 12,708,389 B2
(45) Date of Patent: Aug. 18, 2026

(54) THROMBECTOMY SYSTEMS AND METHODS FOR SAME

(71) Applicant: Surmodics MD, LLC, Eden Prairie, MN (US)

(72) Inventors: Derek Stratton, Bloomington, MN (US); Lucas DeMars, St. Cloud, MN (US); Joseph Duerr, Maple Grove, MN (US); Cara Bjerke, Big Lake, MN (US)

(73) Assignee: Surmodics MD, LLC, Eden Prairie, MN (US)

( * ) Notice: Subject to any disclaimer, the term of this patent is extended or adjusted under 35 U.S.C. 154(b) by 579 days.

(21) Appl. No.: 18/096,874

(22) Filed: Jan. 13, 2023

(65) Prior Publication Data

US 2023/0225749 A1 Jul. 20, 2023

Related U.S. Application Data

(60) Provisional application No. 63/299,796, filed on Jan. 14, 2022.

(51) Int. Cl.
*A61B 17/221* (2006.01)
*A61M 1/00* (2006.01)

(52) U.S. Cl.
CPC ........... *A61B 17/221* (2013.01); *A61M 1/741* (2021.05); *A61M 1/772* (2021.05); *A61B 2217/005* (2013.01)

(58) Field of Classification Search
CPC ................................ A61M 1/77; A61M 1/774
See application file for complete search history.

(56) References Cited

U.S. PATENT DOCUMENTS 4,430,081 A 2/1984 Timmermans
4,673,393 A 6/1987 Suzuki et al.
(Continued)

FOREIGN PATENT DOCUMENTS

WO WO-2004108183 A2 12/2004
WO WO-2008057666 A2 5/2008
(Continued)

OTHER PUBLICATIONS

"International Application Serial No. PCT US2023 010785, International Search Report mailed Jun. 23, 2023", 4 pgs.
(Continued)

*Primary Examiner* — Rebecca E Eisenberg
*Assistant Examiner* — Ted Yang
(74) *Attorney, Agent, or Firm* — Schwegman Lundberg & Woessner, P.A.

(57) ABSTRACT

A thrombectomy system including a delivery catheter configured to support one or more thrombectomy instruments. The delivery catheter includes a delivery catheter hub and a deliver catheter having a collection shaft with a collection lumen. An aspiration flush valve includes an aspiration port, a flushing port and an outlet port in communication with the collection lumen. The outlet port is in selective communication with the aspiration port and the flushing port. A valve operator is movable relative to the aspiration, flushing and outlet ports. The valve operator includes flushing and aspiration configurations. In the flushing configuration the outlet port is in communication with the flushing port. In the aspiration configuration the outlet port is in communication with the aspiration port.

31 Claims, 12 Drawing Sheets

(56) References Cited

U.S. PATENT DOCUMENTS 4,728,319 A * 3/1988 Masch ............... A61B 18/1442 606/177
4,917,668 A 4/1990 Haindl
5,186,714 A * 2/1993 Boudreault ........... A61M 1/774 606/49
5,247,966 A * 9/1993 Stevens ............... F16K 11/0712 137/625.48
5,449,145 A * 9/1995 Wortrich ............... F16K 27/041 D23/245
5,569,164 A * 10/1996 Lurz ..................... A61M 1/774 606/1
5,658,249 A * 8/1997 Beland .................. A61M 1/774 604/35
5,766,191 A 6/1998 Trerotola
5,911,710 A * 6/1999 Barry ................ A61M 39/0693 604/167.04
5,971,956 A * 10/1999 Epstein ............... A61M 1/7413 604/35
6,007,515 A * 12/1999 Epstein ............ A61B 17/00491 604/82
6,287,280 B1 9/2001 Lampropoulos et al.
6,471,667 B1 * 10/2002 Epstein ................ A61M 1/7411 604/35
6,481,462 B2 * 11/2002 Fillmore ............... A61F 5/4405 251/7
6,551,283 B1 4/2003 Guo et al.
7,779,842 B1 * 8/2010 Russo ................... A61M 1/743 128/207.14
7,837,702 B2 * 11/2010 Bates ...................... A61F 2/014 606/127
9,827,084 B2 11/2017 Bonnette et al.
11,298,218 B2 * 4/2022 Montgomery ........ A61F 2/0105
2001/0011162 A1 * 8/2001 Epstein ................. A61M 1/774 604/35
2003/0042186 A1 * 3/2003 Boyle ....................... A61F 2/01 210/136
2004/0082915 A1 * 4/2004 Kadan .................... A61B 1/317 604/164.04
2007/0010796 A1 * 1/2007 Moran ............. A61M 39/0693 604/167.04
2007/0100276 A1 * 5/2007 Fanton ............. A61B 17/32002 604/22
2007/0282303 A1 * 12/2007 Nash .............. A61B 17/320783 604/510
2008/0306499 A1 * 12/2008 Katoh .............. A61B 17/22031 606/159
2010/0268264 A1 10/2010 Bonnette et al.
2014/0207056 A1 * 7/2014 Bono .................... A61M 39/28 604/34
2015/0265299 A1 9/2015 Cooper et al.
2017/0136158 A1 * 5/2017 Culhane .................. A61M 1/79
2019/0255279 A1 * 8/2019 Bagwell ............ A61M 16/0463
2019/0328942 A1 * 10/2019 Lazic .................... A61M 1/774
2019/0381223 A1 * 12/2019 Culbert ................. A61M 1/772
2020/0129282 A1 * 4/2020 Hauser ........... A61B 17/320758
2021/0402076 A1 * 12/2021 Lee ....................... A61M 1/772
2022/0000600 A1 * 1/2022 Montgomery .......... A61F 2/011
2022/0400972 A1 * 12/2022 Mattmueller .......... A61B 5/685
2024/0299151 A1 * 9/2024 Montgomery .......... A61F 2/011

FOREIGN PATENT DOCUMENTS

WO WO-2014043065 A1 3/2014
WO 2023137168 7/2023

OTHER PUBLICATIONS

"International Application Serial No. PCT US2023 010785, Written Opinion mailed Jun. 23, 2023", 11 pgs.
"European Application Serial No. 23740692.1, Communication pursuant to Rule 164(1) EPC mailed Apr. 14, 2025", 17 pgs.
"International Application Serial No. PCT/US2023/010785, International Preliminary Report on Patentability mailed Jul. 25, 2024", 13 pgs.
"International Application Serial No. PCT US2023 010785, Invitation to Pay Additional Fees mailed Mar. 28, 2023", 2 pgs.
"European Application Serial No. 23740692.1, Extended European Search Report mailed Jul. 7, 2025", 14 pgs.
"European Application Serial No. 23740692.1, Response filed Jan. 26, 2026 to Extended European Search Report mailed Jul. 7, 2025", 35 pgs.

* cited by examiner 120
122
110
124
118
108
154
152
150
156
114
130
158
104
112
116
100
148
140
144
102
142
146

150
208
212
152
210
214
104
200
130
206
116

150
210
212
152
214
208
104
200
130
206
116

804
910
908
926
922
802
920
120
806
924
800
122
124
110
904
900
906
902

THROMBECTOMY SYSTEMS AND METHODS FOR SAME

PRIORITY APPLICATIONS

This application claims the benefit of priority to U.S. Provisional Patent Application Ser. No. 63/299,796, filed Jan. 14, 2022, the content of which is incorporated herein by reference in its entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright Surmodics, Inc. of Eden Prairie, Minnesota. All Rights Reserved.

TECHNICAL FIELD

This document pertains generally to guide sheaths and catheters, including, but not limited to guide sheaths and catheters capable of aspiration and delivery of thrombectomy devices and other intravascular devices.

BACKGROUND

Thrombectomy procedures treat thrombus within the vasculature with various instruments. In some examples, one or more capture features, such as a cage, filter or the like are delivered to a treatment site. The capture features separate thrombus from vessel walls, collect thrombus from within the vessel, and capture the thrombus for extraction with the remainder of the thrombus assembly. The capture features are coupled with an associated catheter (e.g., guidewire, tube or the like), for instance at the catheter distal end, forming a capture catheter.

In some examples, the capture features are received within a trumpet catheter. The trumpet catheter includes a deployable trumpet that is in turn received within a sheath catheter. The sheath catheter envelops the trumpet and capture features (of the capture catheter).

The various capture features, trumpet catheter, introducers, delivery catheters or the like (collectively catheters or instruments) are in various examples navigated over guidewires and manipulated relative to each other (e.g., rotated, translated, combinations of both or the like) by clinicians or teams of clinicians to reach a treatment site, deploy capture features at the treatment size, collect thrombus, and retract one or more of the features from the vasculature. In other examples, other treatments are conducted at the treatment site with the catheters or instruments. For instance, fluids, such as thrombolytic medicaments, are delivered through catheters. Additionally, aspiration is in some examples conducted through catheters for instance with syringes, aspiration pumps or the like.

Delivery of the catheters or instruments to the treatment site and conducting treatment are conducted with cooperative operations of multiple components. Cooperative operation includes, but is not limited to, coordinated control (e.g., movement, holding static, moving some components together and maintaining others static, opening or closing valves, administering fluids, aspirating or the like) of a plurality of catheters, sheaths, instruments and associated components by a clinician or team of clinicians to reach, capture, and extract thrombus and the catheters, instruments and components from the vasculature.

OVERVIEW

The present inventors have recognized, among other things, that a problem to be solved includes consolidating various components of a procedure into fewer devices that permits a clinician to readily conduct navigation, delivery, treatment and withdrawal of a thrombectomy system into and from vasculature. For instance, an example thrombectomy procedure implements a variety of guidewires, introducers, catheters, valves (e.g., hemostasis, infusion, aspiration or the like) in addition to mechanical thrombectomy components to reach, treat or capture thrombus (or both), and withdraw thrombus and the instruments from the vasculature. In many examples, two or more clinicians, sometimes a team of clinicians, cooperate to conduct these operations by moving the various components relative to each other (each controlled by a different clinician) or to institute one or more procedures, such as thrombolytic infusion, aspiration, mechanical thrombectomy or the like. For instance, catheters, sheaths, instruments within sheaths (e.g., collection funnel, filters or the like) of thrombectomy systems are manipulated, including translated, rotated or the like, relative to each other to move, deploy, capture thrombus, retract and withdraw thrombus and the various components of the thrombectomy systems. Additionally, valves, pumps or the like are operated to infuse fluids, aspirate thrombus or the like.

The present subject matter can help provide a solution to this problem with a thrombectomy system and associated components that consolidate features of the system into relatively compact profile that is readily operated by one or more clinicians. In one example, the thrombectomy system includes a delivery catheter hub that permits delivery of one or more instruments, such as a thrombectomy catheter. The delivery catheter hub includes a collection catheter (also optionally referred to as a delivery catheter). The collection catheter includes a collection shaft coupled with the delivery catheter hub. In another example, a collection funnel is optionally included and positioned at the distal end of the collection shaft. The collection funnel, where included, operates as one or more of a funnel or ramp for gradually compressing (e.g., collapsing, contracting or the like) deployed thrombectomy elements, such as thrombus collection filters, as the thrombectomy elements are pulled axially into the collection catheter for withdrawal from the body. The radial collapse of thrombus collection filters caused by the collection funnel in one example enhances compression of thrombus captured by the thrombus collection filters. A sheath body is movably coupled with the delivery catheter hub and coupled along the collection shaft. Movement of the sheath body is controlled with an operator on the hub, and the sheath body stores and deploys the collection funnel (e.g., at a treatment site) according to remote movement of the operator at the hub. For example, the operator moves the sheath body proximally to reveal the collection funnel and permit its expansion into the funnel profile.

In another example, the collection catheter coupled with the delivery catheter hub includes a collection lumen (optionally referred to as a delivery lumen) to permit delivery of one or more instruments, such as a thrombectomy catheter, to a treatment site. For instance, the thrombectomy catheter is backloaded through a hemostasis valve of the hub (described herein), and passed through the collection lumen and collection funnel to the treatment site. The collection shaft of the collection catheter optionally serves as sheath for the one or more collection filters of the thrombectomy catheter. As the collection shaft is moved proximally relative to the collection filters the filters are revealed and deploy from the filter shaft of the thrombectomy catheter (e.g., with shape memory materials, bias mechanisms or the like). In another example, a filter catheter having a distal mounted filter (slidably received in the collection shaft) that is optionally positioned proximal to the one or more collection filters to receive the filters. In this configuration, the filter catheter with the collection filters received within the distal mounted filter is withdrawn through the collection lumen.

As further discussed herein, in another example, the delivery catheter hub includes a hemostasis valve including a valve defeater that facilitates delivery and manipulation of instruments relative to the delivery catheter hub. The hemostasis valve includes a valve diaphragm that minimizes leaking through the valve (e.g., body fluids, infused fluids or the like). The hemostasis valve further includes a valve defeater with a spanning element. The delivery catheter hub, in an example, includes a defeater operator that permits movement of the valve defeater and its spanning element. For instance, a clinician operating the delivery catheter hub has access to and is able to actuate the defeater operate to move the spanning element of the valve defeater into an interconnecting configuration. In the interconnecting configuration the spanning element penetrates the valve diaphragm and a spanning lumen therein accordingly extends through the penetrated valve diaphragm. The spanning lumen is aligned with the collection lumen of the collection catheter.

Instruments, such as the thrombectomy catheter are readily delivered through the defeated (e.g., spanned) hemostasis valve by way of the spanning lumen and into the collection lumen. Because the valve diaphragm is deflected away by the spanning element from instruments extending through the valve the instruments are easily manipulated through the delivery catheter hub including, but not limited to, translated, rotated or the like within the spanning lumen and the collection lumen. Likewise, the deflection of the valve diaphragm by the defeater avoids or limits engagement between the instruments and the valve diaphragm thereby avoiding abrasion of the valve diaphragm otherwise caused by moving instruments and improving sealing when the valve diaphragm closes. The valve diaphragm is deformed away from the instrument within the spanning lumen and does not engage with the instrument in a manner that frustrates mobility. Accordingly, the clinician may readily move the instrument as needed without interference from the hemostasis valve and the delivery catheter hub. Optionally, distal movement of an instrument is configured to bias the spanning element distally and the valve diaphragm is automatically deflected by the spanning element to permit eased distal movement of the instrument.

The hemostasis valve optionally includes a biasing element. Upon release of the valve defeater or, optionally proximal retraction of an instrument in the spanning lumen, the valve defeater is moved to an arrested configuration and the spanning element is retracted from the valve diaphragm to permit closure of the diaphragm. In one example, release of the valve defeater and arresting of the spanning element from the valve diaphragm with an instrument in the hemostasis valve permits the valve diaphragm to contract around the instrument and provide a seal therearound. Optionally, the instrument is held in place by the valve diaphragm. If eased manipulation is specified the valve defeater is actuated again to place the spanning element in the interconnecting configuration with the element spanning the valve diaphragm.

In another example, the thrombectomy system includes an aspiration flush valve, for instance coupled with a side port or side channel of the delivery catheter hub. The aspiration flush valve consolidates flushing (e.g., for infusion) and aspiration. Additionally, the aspiration flush valve permits the clinician to toggle between each of these functions and optionally secure the aspiration flush valve for continuous aspiration while freeing the clinician to conduct other operations with the thrombectomy system. In one example, the aspiration flush valve is proximate to the delivery catheter hub of the thrombectomy system. For instance, the aspiration flush valve is within 3 inches or less, 6 inches or less, 12 inches or less or the like to permit ready access and actuation of the valve by the clinician using the same hand that holds the delivery catheter hub (or permitting ready use of the other hand of the clinician).

The aspiration flush valve includes a valve body having an outlet port configured to communicate with the collection lumen of the collection catheter. The valve body further includes aspiration and flushing ports selectively in communication with the outlet port. A valve operator is movably coupled with the valve body, and transitions the aspiration flush valve between a flushing configuration (including infusion) and an aspiration configuration (and optionally a locked aspiration configuration). The valve operator includes an operator shaft in one example having a flush layer with a flush lumen and an aspiration layer having an aspiration lumen. Operation of the valve operator (e.g., depression) moves the flush layer and aspiration layers into selective alignment with the ports of the valve body. Accordingly, with the flush layer aligned the flush port is in communication with the outlet port through the flush lumen. With actuation of the valve operator the flush layer is misaligned with the ports and the aspiration layer is moved into alignment to interconnect the aspiration port with the outlet port. Optionally, the valve operator is secured to permit continuous communication between the aspiration and outlet ports.

In operation the clinician is readily permitted to toggle between the flushing and aspiration configurations proximate to the delivery catheter hub (e.g., with single handed operation). Toggling between the flushing and aspiration configurations permits various applications of pressure, for instance to agitate and free plugs, blocks or the like of thrombus in the thrombectomy system. Securing of the aspiration flush valve in the locked aspiration configuration permits the continuous application of negative pressure (e.g., vacuum) to permit ongoing aspiration.

In one example, the clinician connects a vacuum syringe to the aspiration port and withdraws the plunger thereby generating a volume of decreased pressure in the syringe. Selective or continuous operation of the aspiration flush valve with the valve operator permits the application of negative pressure from the readied vacuum syringe, and locates the operation of the aspiration flush valve proximate to the delivery catheter hub. Accordingly, the clinician is provided with a ready source of aspiration that is controlled near other controlled features of the thrombectomy system (e.g., the hemostasis valve, thrombectomy catheter, collection catheter and collection funnel or the like).

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
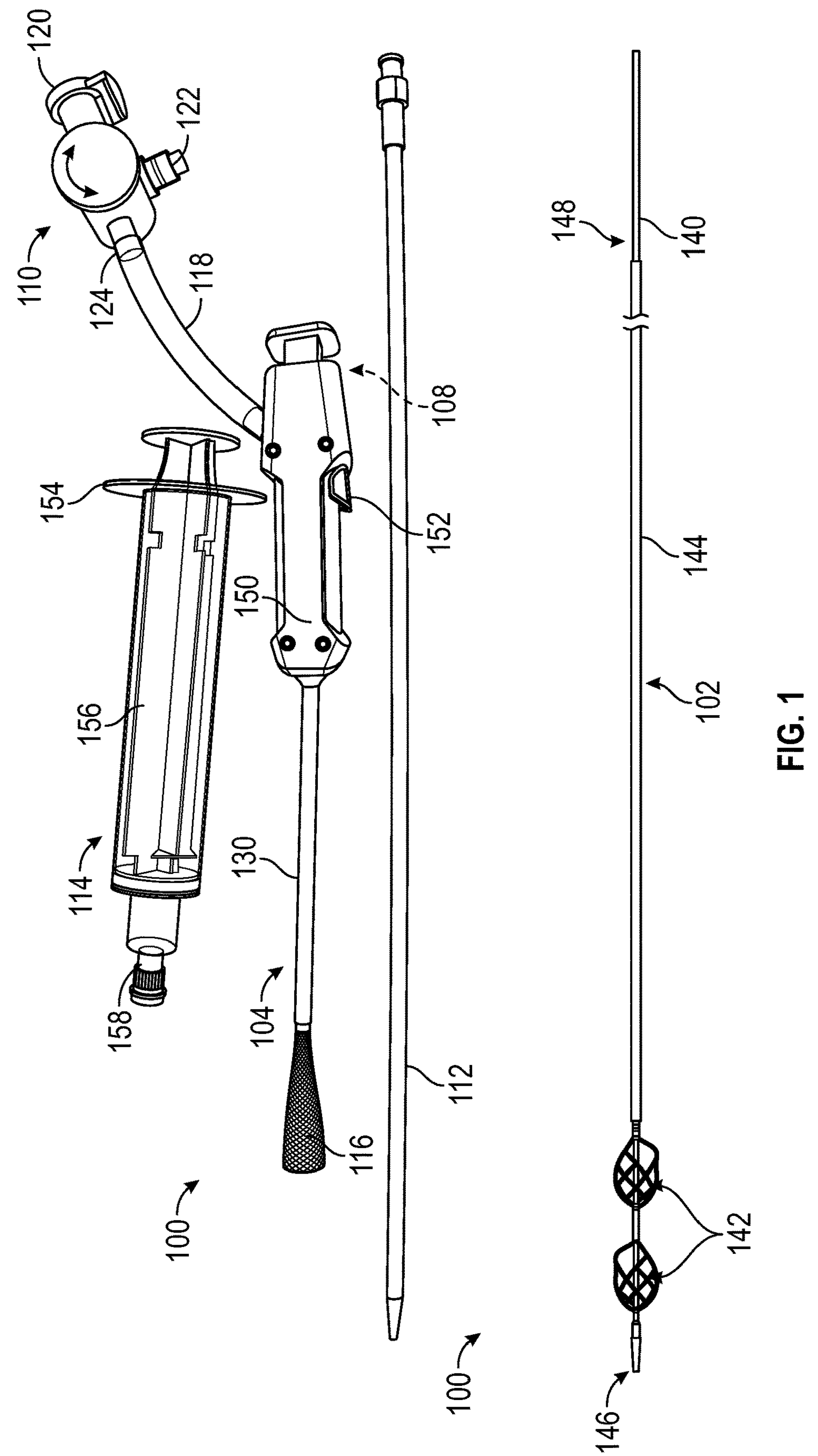
FIG. 1 is a perspective view of one example of a thrombectomy system.

FIG. 1 is a perspective view of an example thrombectomy system 100 including thrombectomy catheter 102 and a delivery catheter 104 configured to deliver the thrombectomy catheter including one or more thrombectomy elements, such as collection filters 142. The delivery catheter 104 is constructed with various diameters, and in examples is constructed in a range of between 8 and 20 French. The thrombectomy system 100 further includes one or more additional components, such as, an aspiration flush valve 110, aspiration source 114 (e.g., a vacuum syringe, pump or the like), dilator 112 or the like.

Referring first to the delivery catheter 104, the catheter includes a delivery catheter hub 150. As described herein the delivery catheter hub 150 interconnects various components of the thrombectomy system 100 and consolidates operations to assist the clinician in conducting procedures while minimizing additional personnel or frustrating manipulation of multiple disparate (and sometimes remote) pieces of equipment.

The delivery catheter hub 150 includes a sheath body 130 movably coupled with the hub 150. For example, the sheath body 130 is coupled with an operator 152 movably coupled with the delivery catheter hub 150. As described herein, actuation of the operator 152 moves the sheath body 130 and accordingly reveals and conceals a collection funnel 116 of the delivery catheter hub 150. The collection funnel 116 is coupled with a collection shaft (see FIG. 2), and the collection funnel 116 and the collection shaft are received within the sheath body 130.

The delivery catheter hub 150 further includes a hemostasis valve 108, shown in FIG. 1 with a broken line arrow. The hemostasis valve closes the interior of the delivery catheter 104 including a collection lumen (201 in FIG. 2) of the collection shaft (interior to the sheath body 130). As further described herein, the hemostasis valve includes a valve defeater configured to bypass a valve diaphragm of the valve 108. The valve defeater is actuated by the clinician and permits the ready delivery and movement of instruments through the hemostasis valve. Resistance to motion, otherwise caused by the valve diaphragm, is selectively overcome by the valve defeater to ease delivery and movement of instruments into and through the delivery catheter 104.

Referring again to FIG. 1, an aspiration flush valve 110 is coupled with a side channel 118 of the delivery catheter hub 150. The aspiration flush valve 110 includes a plurality of ports including an outlet port 124 coupled with the hub 150 and aspiration and flushing ports 120, 122. As described herein the aspiration flush valve 110 includes a valve operator configured to transition the valve between aspiration and flushing configurations (and optionally a locked aspiration configuration), for instance to provide one or more of flushing, aspiration, pulsed flushing (including infusions), pulsed aspiration, and ongoing or continuous aspiration. The valve operator is proximate to the delivery catheter hub 150 to consolidate flushing and aspiration control for the clinician conducting thrombectomy procedures with the thrombectomy system 100. For instance, the aspiration flush valve 110 is within 3 inches or less, 6 inches or less, 12 inches or less or the like to permit ready access and actuation of the valve 110 by the clinician using the same hand that holds the delivery catheter hub 150 (or permitting ready use of the other hand of the clinician).

In another example, the thrombectomy system 100 includes an aspiration source 114, such as, but not limited to, a vacuum syringe, vacuum lock syringe, aspiration pump or the like. One example of an aspiration source 114 is shown in FIG. 1, and includes a vacuum syringe. The vacuum syringe includes a syringe body 154 and a syringe plunger 156 received therein. In one example, the syringe plunger 156 is retracted while a syringe port 158 is closed or coupled with the aspiration port 120 of the aspiration flush valve 110. Retraction of the plunger 156 generates a negative pressure in syringe body 154. As described herein, operation of the aspiration flush valve 110 selectively opens the delivery catheter 104, instruments in the catheter, vasculature or the like to the syringe body 154 and accordingly aspiration is conducted. The clinician readily controls application of aspiration with the valve operator of the aspiration flush valve 110.

FIG. 1 shows an example of a thrombectomy catheter 102. The thrombectomy catheter 102 is a representative thrombectomy device for use with the delivery catheter 104 such as shown in U.S. Pat. No. 9,827,084 (filed Oct. 27, 2008; entitled Intravascular Guidewire Filter System for Pulmonary Embolism Protection and Embolism Removal of Maceration) and U.S. application Ser. No. 17/896,589 (filed Aug. 26, 2022; entitled Thrombectomy Capture System), both of which are incorporated by reference. The delivery catheter 104 is optionally sized to receive and cooperate with other thrombectomy catheters that are delivered intravascularly including, but not limited to, mechanical, fluid, fluid-mechanical thrombectomy catheters or the like.

The thrombectomy catheter 102 is navigated to a treatment location, for instance through the delivery catheter 104 including the hub 150 and a collection lumen of the collection shaft 200. In one example, a filter shaft 140 of the thrombectomy catheter 102 includes a guidewire having one or more collection filters 142 coupled with the shaft 140. In another example, the filter shaft 140 includes a tubular shaft coupled with the one or more collection filters 142, and the filter shaft 140 is optionally navigated along a guidewire, catheter or the like received in the filter shaft 140. In either example, the thrombectomy catheter 102 is cooperatively used with the delivery catheter 104 having the collection catheter 200 (and collection lumen 201) described herein.

In the example shown in FIG. 1, two collection filters 142 are coupled with the filter shaft 140. The collection filters 142 are show in a deployed configuration. Optionally, the collections filters 142 are compressible toward the filter shaft and held in place during navigation and delivery through vasculature. For instance, the collection filters are anchored to the filter shaft 140 at their respective distal ends, and slidably coupled with the filter shaft 140 at their proximal ends. Exposure of the collection filters 142 (e.g., through retraction of a sheath or distal movement relative to a sheath) permits the filters 142 to expand, for instance with the respective proximal ends sliding over the filter shaft 140 distally. Optionally, the collection filters 142 are constructed with shape memory materials or the like that bias the filters 142 to the deployed configuration shown in FIG. 1. In another example, the thrombectomy catheter couples the collection filters 142 with the filter shaft 140 and also couples the filters (e.g., opposed ends relative to the coupling the filter shaft) with a movable component, such as an overlying catheter. Cooperative movement of the overlying catheter (e.g., distally) relative to the filter shaft 140, in this example, compresses the end portions of the collection filters 142 together and thereby expands the filters 142 into the deployed configuration shown in FIG. 1. In at least one example, the thrombectomy catheter 102 can be provided with a filter catheter, including its own deployable tapered filter, such as a trumpet, for receiving the collection filters 142 prior to retraction of the collection filters 142 into the collection shaft 200. In this example, the filter catheter includes its own tapered filter for covering the collection filters 142 during capture within the collection shaft 200 and to decrease loss of thrombus material during compression and dehydration of thrombus captured in the collection filters 200.

In one example, the delivery catheter 104, such as the collection shaft 200 (see FIG. 2) or sheath body 130, constrains the collections filters 142 from expanding. In another example, the thrombectomy catheter 102 includes a filter sheath 144 movable relative to the filter shaft 140 and the filters 142. Retraction of the filter sheath 144 reveals the collection filters 142 and permits their expansion to the deployed configuration shown in FIG. 1.

Figure 2:
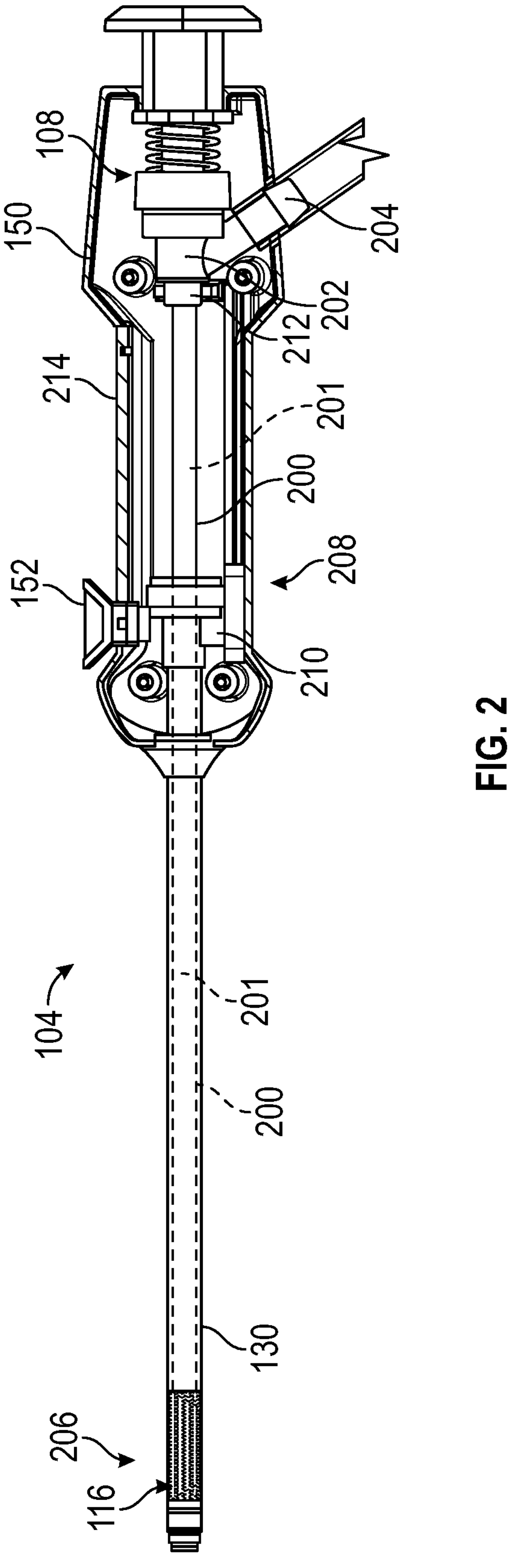
FIG. 2 is a partial sectional view of a delivery catheter.

FIG. 2 shows one example of the delivery catheter 104, for instance, with an optional collection funnel 116 in a concealed or stowed configuration. The delivery catheter hub 150 is shown in a partially sectioned view, for instance, with the interior of the delivery catheter hub 150 exposed. As previously described, the delivery catheter 104 includes a sheath body 130 coupled with the delivery catheter hub 150. As shown in FIG. 2, the sheath body 130 is, in one example, moveably coupled with the delivery catheter hub 150, for instance, by way of a sheath shuttle 210. The sheath shuttle 210 is coupled with an operator 152 provided along an exterior of the delivery catheter hub 150. The operator 152 is actuated by a clinician holding the delivery catheter hub 150, for instance, during a thrombectomy procedure. Movement of the operator 150 relative to the delivery catheter hub 150 (e.g., along an operator track 214) moves the operator 150, the sheath shuttle 210 and the sheath body 130 relative to the delivery catheter hub 150 as well as the collection shaft 200 (optionally referred to as a delivery shaft) extending from the delivery catheter hub 150.

As further shown in FIG. 2, the collection shaft 200 (optionally referred to as a delivery shaft of a delivery catheter) extends from a collection seat 212 proximate to a proximal portion 208 of the delivery catheter 104, and for example provided within the delivery catheter hub 150. The collection shaft 200 extends toward a distal portion 206 of the delivery catheter 104. As further shown in FIG. 2, for instance in broken lines, the collection funnel 116 is in a stowed configuration within the sheath body 130. As previously described, the collection funnel 116 is coupled with the collection shaft 200 and, with the sheath body 130 in the position shown, the collection funnel 116 is compressed and in a stowed configuration. If deployment of the collection funnel 116 is desired, for instance, during a thrombectomy procedure to facilitate the capture of thrombus the sheath body 130 is retracted with distal movement of the operator 150. Distal movement of the operator 152 correspondingly moves the sheath body 130 and reveals the collection funnel 116 thereby permitting the collection funnel 116 to deploy into the deployed configuration shown in FIGS. 3A and 3B.

The delivery catheter 104 in other examples includes the collection shaft 200 without the collection funnel 116, and optionally is without the sheath body 130. In this example, the collection shaft 200 is optionally referred to as a delivery shaft 200, and the collection lumen 201 is optionally referred to as a delivery lumen 201. In other examples, the delivery catheter 104 includes the collection funnel 116, sheath body 130 or the like, and in those examples the collection shaft 200 may also be referred to as a delivery shaft 200 having a delivery lumen 201.

As further shown in FIG. 2, in this example, the delivery catheter hub 150 includes the hemostasis valve 108 previously described with regard to FIG. 1. In this view, the hemostasis valve 108 is revealed in the sectional view of the hub 150. The hemostasis valve 108, as described herein, is configured to communicate with other portions of the delivery catheter 104, for instance, with a collection lumen within the collection shaft 200. One or more instruments, such as the thrombectomy catheter 102 shown in FIG. 1, are delivered through the hemostasis valve 108 by way of a valve defeater described herein. the hemostasis valve 108 is shown at the proximal portion 208 of the delivery catheter 104. In one example, the hemostasis valve 108 includes one or more lumens, such as a spanning lumen, aligned with the collection lumen of the collection shaft 200. Accordingly, as instruments are delivered through the hemostasis valve 108, they are aligned with the collection shaft 200 and thereby readily delivered through the delivery catheter 104 toward the distal portion 206, for instance, for delivery through the collection funnel 116.

As further shown in FIG. 2, the delivery catheter hub 150, in this example, includes a side port 204. The side port 204 extends into a catheter manifold 202 including in communication with a collection lumen 201 of the collection shaft 200. The side port 204 is, in one example, coupled with an aspiration flush valve such as the aspiration flush valve 110 shown in FIG. 1. Accordingly, one or more of infusions, aspiration or the like are transmitted through the side port 204 to the catheter manifold 202 and down the length of the delivery catheter 104, for instance, in the collection lumen 201 of the collection shaft 200. In another example, the hemostasis valve 108 cooperates with the side port 204 and the aspiration flush valve 110 to seal the interior of the delivery catheter 104 and accordingly ensure flushing and aspiration are conducted along the collection shaft 200 and the hemostasis valve 108 prevents interaction with an exterior environment.

Figures 3A, 3B:
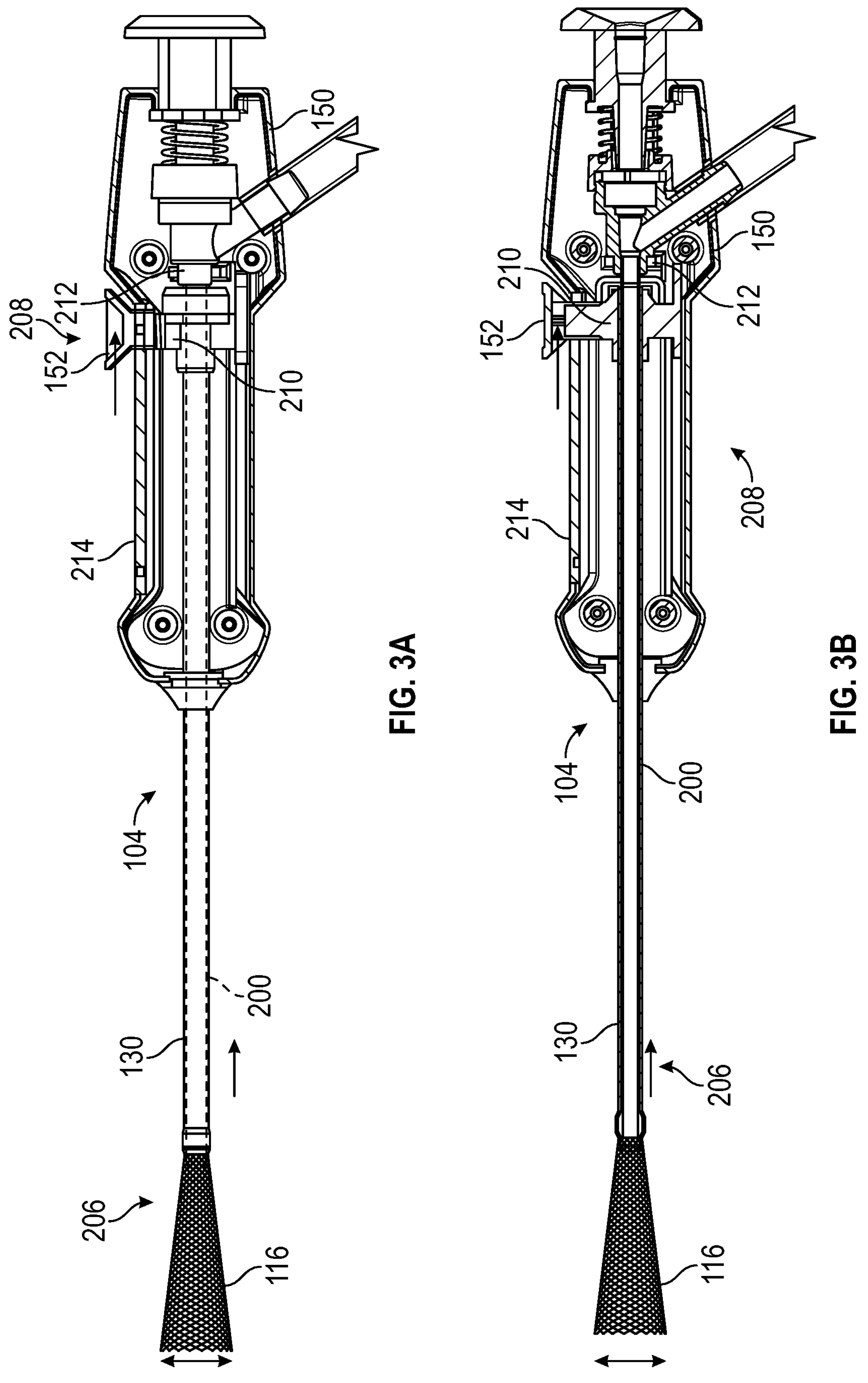
FIG. 3A is a partial sectional view of the delivery catheter of FIG. 2 with an example collection funnel in a deployed configuration.
FIG. 3B is a sectional view of the delivery catheter of FIG. 2 with the collection funnel in a deployed configuration.

FIGS. 3A and 3B show partial sectional and sectional views, respectively, of the delivery catheter 104 with the collection funnel 116 in the deployed configuration. In the views shown in FIGS. 3A and 3B, the operator 152 is moved in a distal fashion relative to the view previously shown in FIG. 2. Accordingly, with distal movement of the operator 152, the sheath shuttle 210 and the sheath body 130 are correspondingly moved distally. The collection funnel 116 is reveal with distal movement of the sheath body 130 and permitted to passively or actively deploy. In one example, the collection funnel 116 is constructed with one or more shape memory materials, biased materials or the like configured to automatically expand the collection funnel 116 to the deployed configuration shown in FIGS. 3A and 3B upon revelation. This is an example of passive deployment of the collection funnel 116. In another example, the collection funnel 116 is coupled with each of the collection shaft 200 and the sheath body 130, and relative movement between the shaft and body reveals the collection funnel 116 and provides outward directed bias (e.g., active deployment) to expand the collection funnel 116. Conversely, movement of the sheath body 130 distally biases the collection funnel 116 to contract or collapse.

As shown in FIGS. 3A and 3B, as the sheath shuttle 210 is moved distally, the underlying collection shaft 200 is static, for instance is coupled to the static collection shaft seat 212. Accordingly, the sheath body 130 is slid relative to the collection shaft 200 to thereby reveal the collection funnel 116. In another example, the collection funnel 116 is coupled with each of the collection shaft 200 and the sheath body 130. For instance, a first end of the collection funnel 116 is coupled with the collection shaft 200 and a second end of the funnel 116 is coupled with the sheath body 130. In such an example, cooperative movement of the sheath body 130 relative to the collection shaft 200 biases the collection funnel 116 outwardly, for instance, to actively expand the collection funnel. Optionally, the collection funnel 116 is everted (turned at least partially inside out) to transition the funnel 116 into the deployed configuration shown in FIGS. 3A and 3B.

Figure 4:
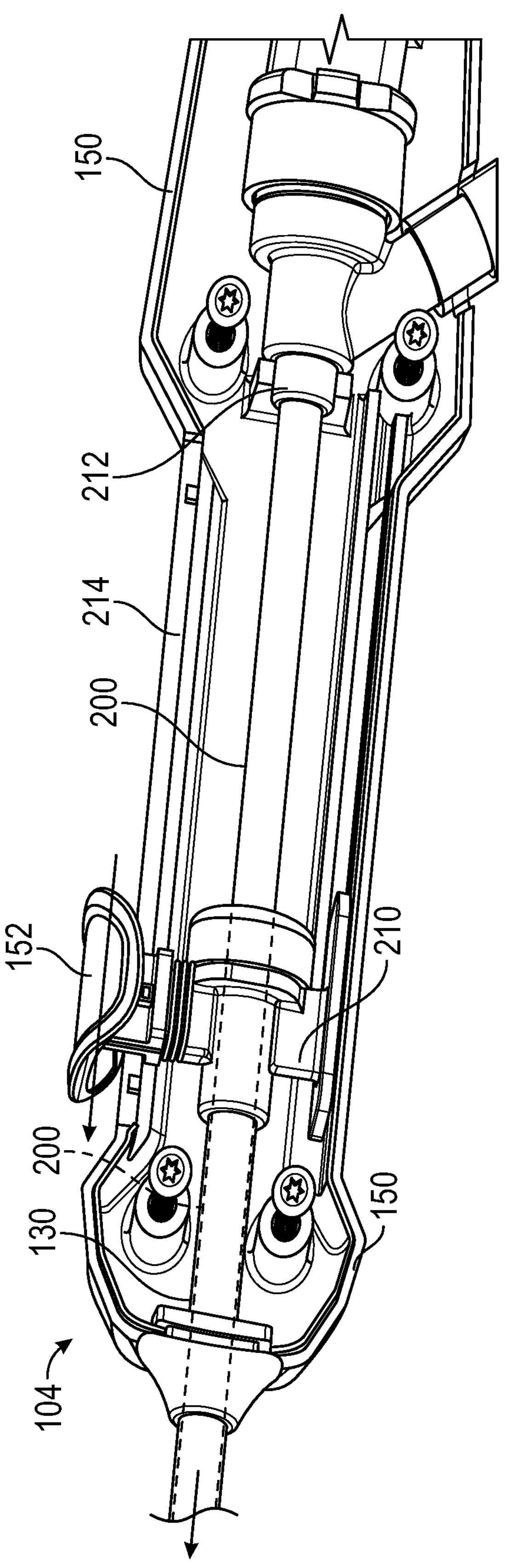
FIG. 4 is a partial sectional view of the delivery catheter hub of the delivery catheter with an actuated operator to compress the collection funnel to a stowed configuration.

Referring now to FIG. 4, the delivery catheter hub 150 is shown again in a partially sectioned view. In this example, the operator 152 is moved in a distal manner toward the distal portion 206 of the delivery catheter 104 shown, for instance, in FIGS. 3A and 3B. Distal movement of the operator 152 moves the sheath shuttle 210 and the sheath body 130 coupled with the sheath shuttle 210 relative to the collection shaft 200. Distal movement of the sheath body 130 moves the sheath body 130 over the collection funnel 116, shown in FIGS. 3A and 3B, and compresses or sheaths the collection funnel 116 to the stowed configuration shown in FIG. 2. The operator or clinician is thereby able to move the operator 152 in a reciprocal fashion proximally and distally within the operator track 214 to accordingly move the sheath body 130 and deploy and stow the collection funnel 116 as specified. For instance, the clinician may, in one example, deploy the collection funnel 116 in an initial position; then stow the collection funnel 116, for instance, to reposition the delivery catheter 104; and then redeploy the collection funnel 116. Each of the deployment and stowing operations are conducted with movement of the operator 152. In another example, where retraction of the delivery catheter 104, for instance, from the vasculature is desired, the sheath body 130 is distally moved with the operator 152 to sheath the collection funnel 116 and thereby narrow the profile of the delivery catheter 104 to permit retraction of the delivery catheter 104 through the vasculature.

Figure 5:
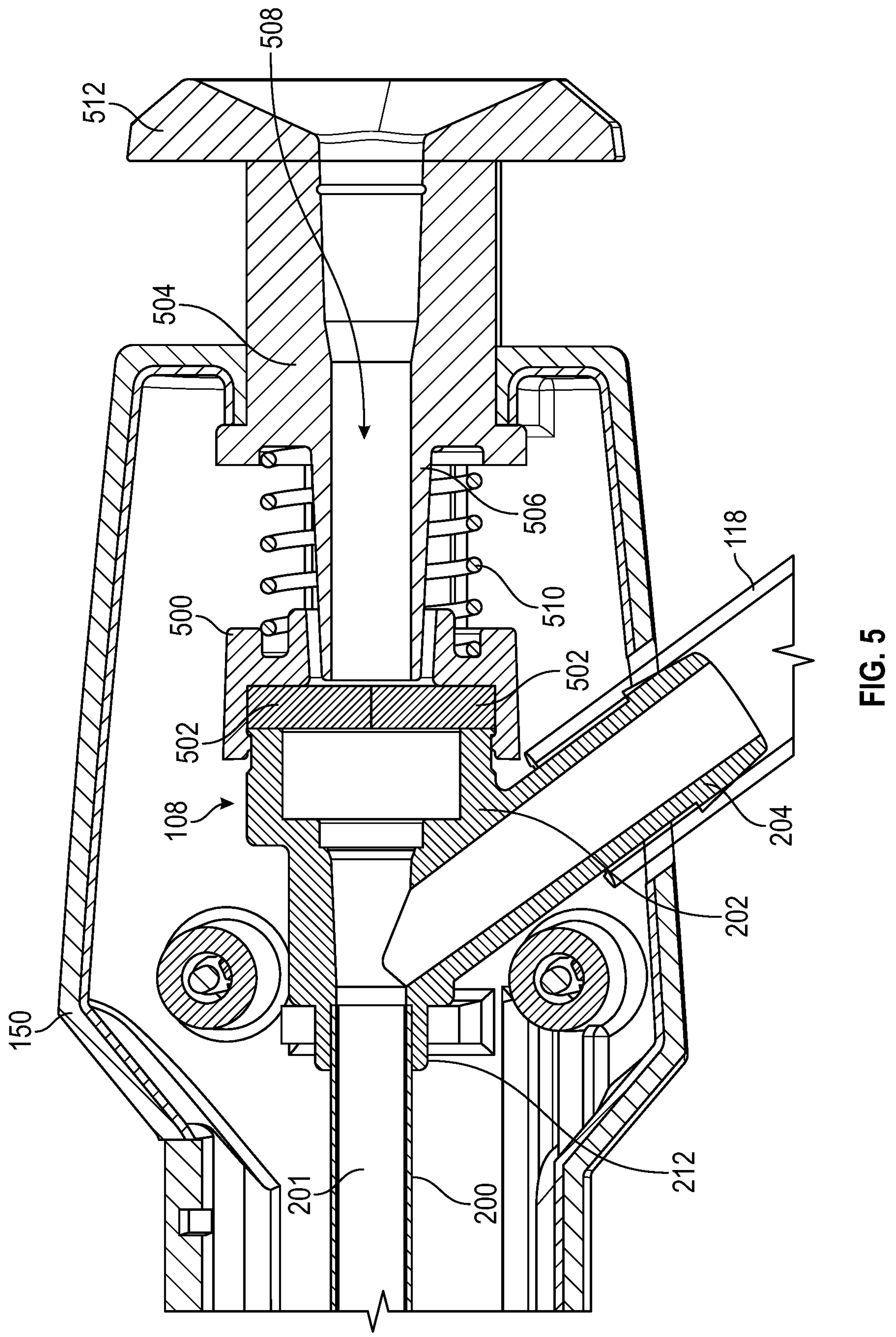
FIG. 5 is a sectional view of an example hemostasis valve having a valve defeater.

FIG. 5 is another sectional view of the delivery catheter hub 150 of the delivery catheter 104. The hemostasis valve 108 is shown in section in FIG. 5. In this example, the hemostasis valve 108 is in an arrested configuration, for instance, with a valve defeater 504 retracted from the valve diaphragm 502. The valve diaphragm 502 is a deformable membrane extending across a portion of the catheter manifold 202 to provide a sealed or closed configuration of the hemostasis valve 108 relative to the collection shaft 200 and the associated collection lumen 201. In one example, the hemostasis valve 108 is provided as a portion or component of the catheter manifold 202. In another example, a valve housing 500 is coupled with the remainder of the catheter manifold 202 and couples the valve diaphragm 502 to the manifold 202. In one example, the valve diaphragm 502 includes, but is not limited to, a split membrane constructed with one or more of rubber or the like that extends across the catheter manifold 202 to close the collection lumen 201 within the collection shaft 200.

As further shown in FIG. 5, an optional side port 204 is coupled with the aspiration flush valve 110 shown in FIG. 1 is provided. A side channel 118 extends from the side port 204 to the aspiration flush valve 110 as described herein. As shown, the side port 204 extends into the catheter manifold 202 and provides a juncture with the lumens of the delivery catheter 104 including, for instance, the collection lumen 201 within the collection shaft 200 and the spanning lumen 508 of the hemostasis valve 108 extending toward the catheter manifold 202.

Referring again to FIG. 5, a valve defeater 504 is moveably coupled with the remainder of the hemostasis valve 108, such as the valve housing 500. In the example shown in FIG. 5, the valve defeater 504 is shown in an arrested configuration with a spanning element 506 of the valve defeater 504 retracted from the valve diaphragm 502 and accordingly not penetrating the valve diaphragm 502. As described herein the spanning element 506 is a tubular element, cage (e.g., perforated, mesh) or the like configured to selectively penetrate the valve diaphragm 502.

As further shown in FIG. 5, the valve defeater 504 includes the spanning element 506 and a spanning lumen 508 extending through the spanning element 506. In another example, the spanning lumen 508 extends through a defeater operator 512 of the valve defeater 504. As described herein, the defeater operator 512 is, in one example, a depressible feature such as a button, bumper or the like configured for actuation by the clinician to overcome, for instance, a bias provided by a biasing element 510 and deliver or drive the spanning element 506 into and through the valve diaphragm 502.

Figure 6:
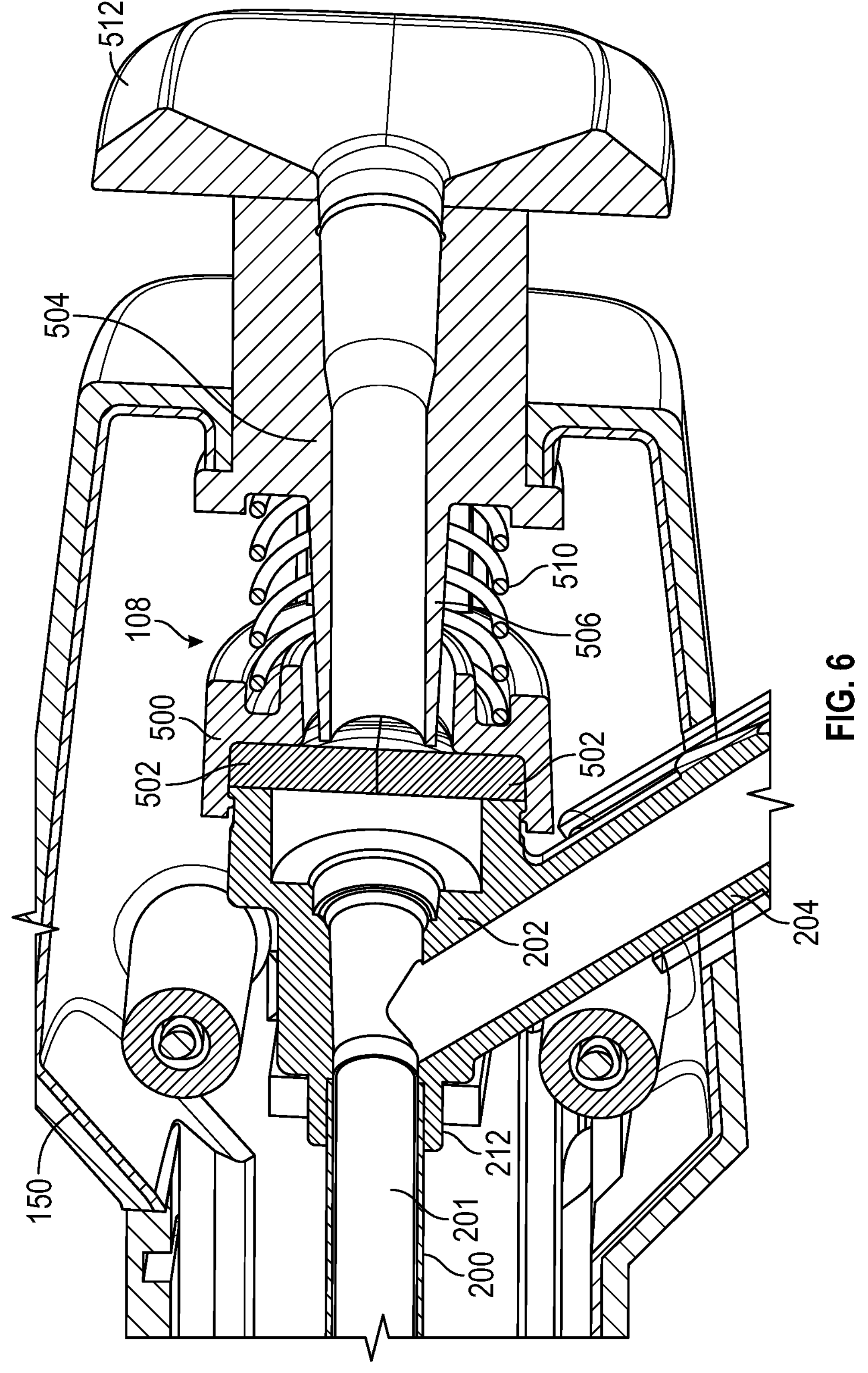
FIG. 6 is a perspective sectional view of the hemostasis valve of FIG. 5 showing a defeater operator, spanning element, and spanning lumen of the valve defeater.

FIG. 6 shows a perspective sectional view of the delivery catheter hub 150 previously described and shown in FIG. 5. In this example, the defeater operator 512 is shown again, for instance, with the spanning lumen 508 extending through the operator of the valve defeater 504. As further shown in FIG. 6, the defeater operator 512 is, in one example, a button or other feature configured to move relative to the remainder of the delivery catheter hub 150, for instance, in a distal direction that moves the spanning element 506 into an interconnecting configuration through the valve diaphragm 502. As shown in FIGS. 5 and 6, the collection lumen 201 of the collection shaft 200 is aligned with the spanning lumen 508 of the spanning element 506 of the valve defeater 504. In the interconnecting configuration (see FIG. 7) the spanning lumen 508 provides a continuous interface (including a near continuous interface) between the collection lumen 201 of the collection shaft 200 and the valve defeater 504 to permit delivery and manipulation of instruments between the lumens 201, 508.

Figure 7:
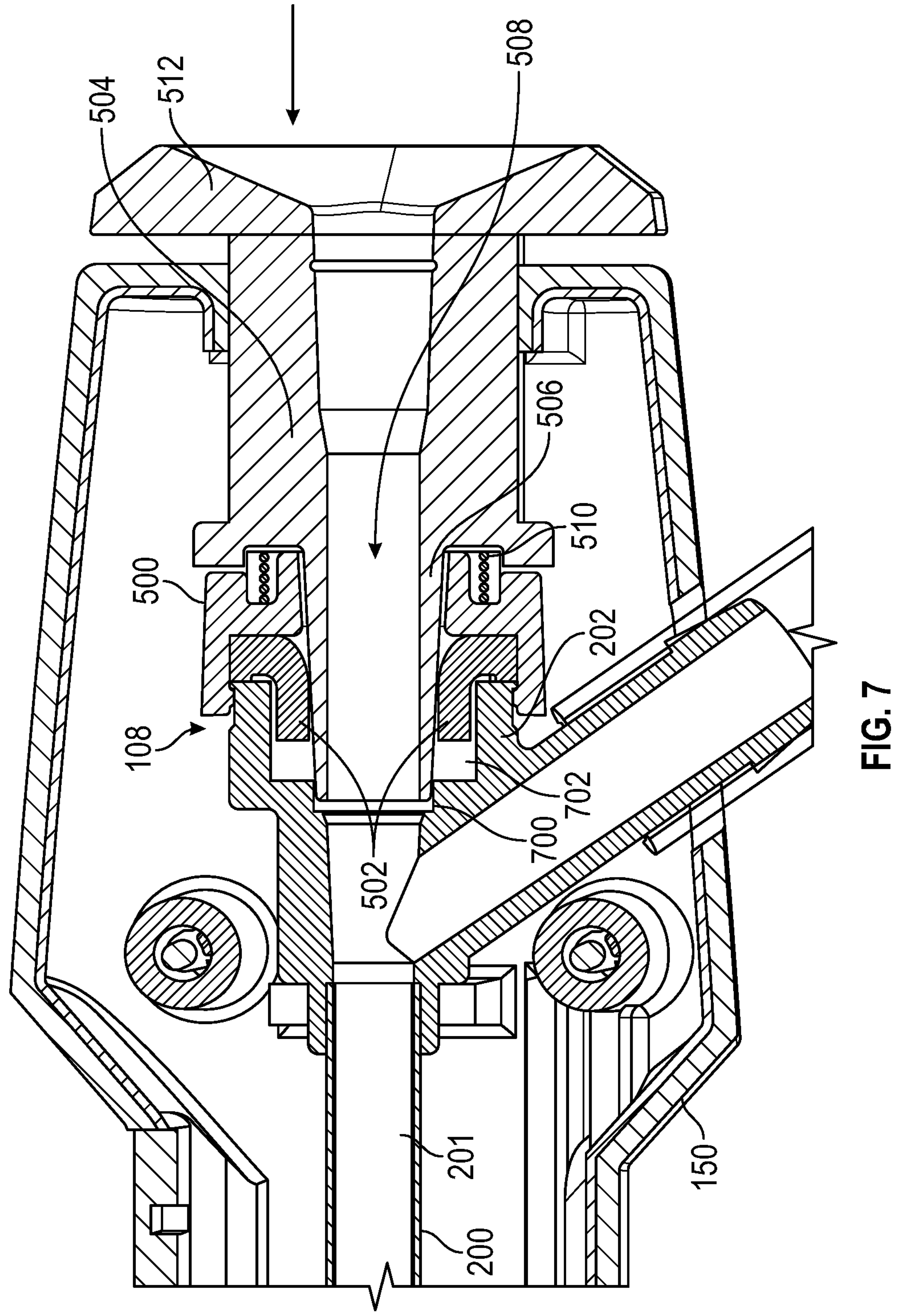
FIG. 7 is a sectional view of the hemostasis valve of FIG. 5 with the spanning element of the valve defeater in an interconnecting configuration.

FIG. 7 shows another cross-sectional view of a portion of the delivery catheter hub 500 including the hemostasis valve 108 in an interconnecting configuration. The valve defeater 504 is moved to the interconnecting configuration through movement of the defeater operator 512 distally relative to the configuration shown in FIGS. 5 and 6. In the example shown in FIG. 7, the spanning element 506 having the spanning lumen 508, is driven across the valve diaphragm 502. The valve diaphragm 502, including leaflets, septum or the like, is deformed and isolated from each of the collection lumen 201 and the spanning lumen 508 (and instruments therein). The spanning element 506 extends into the catheter manifold 202 and toward the collection lumen 201 of the collection shaft 200. As shown in FIG. 7, the spanning lumen 508 is, in this example, aligned with the collection lumen 201 of the collection shaft 200 while the valve diaphragm 502 is isolated from or spaced from each of the spanning lumen 508 and the collection lumen 201. By delivering the spanning element 506 across the valve diaphragm 502 with the valve defeater 504, the valve diaphragm 502 is isolated from instruments delivered through the spanning lumen 508 and collection lumen 201 of the collection shaft 200. Accordingly, instruments within the lumens 201, 508 readily move (translate, rotate or the like) within the corresponding lumens without interference from the valve diaphragm 502. Accordingly, with operation of the valve defeater 504, the clinician is readily able to move one or more instruments into and through the delivery catheter 104 and also conduct eased translational and rotational movement of the instruments, for instance, during thrombectomy procedures while resistance otherwise provided by the valve diaphragm 502 is minimized (e.g., eliminated, decreased or the like).

As further shown in FIG. 7, in one example, the hemostasis valve 108 includes a biasing element 510. The biasing element 510 is shown in an expanded configuration in FIGS. 5 and 6 and in a compressed configuration in FIG. 7. In one example, the biasing element 510 opposes movement of the valve defeater 504 into the interconnecting configuration, for instance, to span the valve diaphragm 502. Accordingly, the default or initial configuration of the hemostasis valve 108 is the arrested configuration with the spanning element withdrawn relative to the interconnecting configuration (e.g., with the spanning element 506 extending through the valve diaphragm 502 as shown in FIG. 7). If defeating of the valve diaphragm 502 is specified, the clinician distally moves the defeater operator 512, for instance, with finger or hand applied pressure applied to the defeater operator 512 (shown with the arrow in FIG. 7) to distally move the spanning element 506 into and through the valve diaphragm 502 and correspondingly moving the valve diaphragm 502 into the deformed configuration shown in FIG. 7.

In one example, during deformation the valve diaphragm 502 is moved into a deformation cavity 702 formed in the catheter manifold 202, and the deformation cavity 702 is configured to retain the valve diaphragm 502 therein and permit ready deformation of the diaphragm 502 when the interconnecting configuration with the spanning element 506 is specified. Optionally, the catheter manifold 202 further includes an element seat 700 configured to receive the spanning element 506 and provide a smooth interface between the valve defeater 504 spanning lumen 508 and the collection lumen 201 of the collection shaft 200. In another example, the deformation cavity 702, as well as the surrounding catheter manifold 202, brace the valve diaphragm 502 in the deformed configuration shown in FIG. 7 and provides a snug engagement between the spanning element 506 and the valve diaphragm 502. The snug engagement provided with the catheter manifold 202, cavity 702 and the spanning element 506 retains the spanning element 506 in the arrested configuration shown in FIG. 7, for instance with a friction fit that counters bias from the biasing element 510.

In another example, the bias from the biasing element 510 readily overcomes frictions between deformed valve diaphragm 502 and the spanning element 506 upon release of the defeater operator 512 to ensure the valve defeater 504 is moved proximally into the arrested configuration to release the valve diaphragm 502 for sealing. In another example, the spanning lumen 508 of valve defeater 504 includes a tapering profile to facilitate the delivery or introduction of one or more instruments through the valve defeater 504 and into the collection lumen 201 of the collection shaft 200. Optionally, the tapered spanning lumen 508 (e.g., the walls of the spanning element 506 surrounding the lumen 508) passively engage with instruments delivered therethrough. The passive engagement optionally includes incidental friction, interference or the like and accordingly the engagement transmits some motion of the instrument to the valve defeater 504. In one example, distal movement of the instrument is transmitted to the valve defeater 504 to assist with movement of the spanning element 506 through the valve diaphragm 502 into the interconnecting configuration. Stated another way, in one example, introduction of an instrument into the hemostasis valve 108, for instance, through the valve defeater 504, such as the spanning lumen 508, biases the defeater operator 512 into the interconnecting configuration. Accordingly, in such an example, the introduction of the instrument to the hemostasis valve 108 ensures the valve diaphragm 502 is spanned with the spanning element 506 and automatically deformed to bypass or isolate instruments from further interference by the diaphragm 502.

Figure 8:
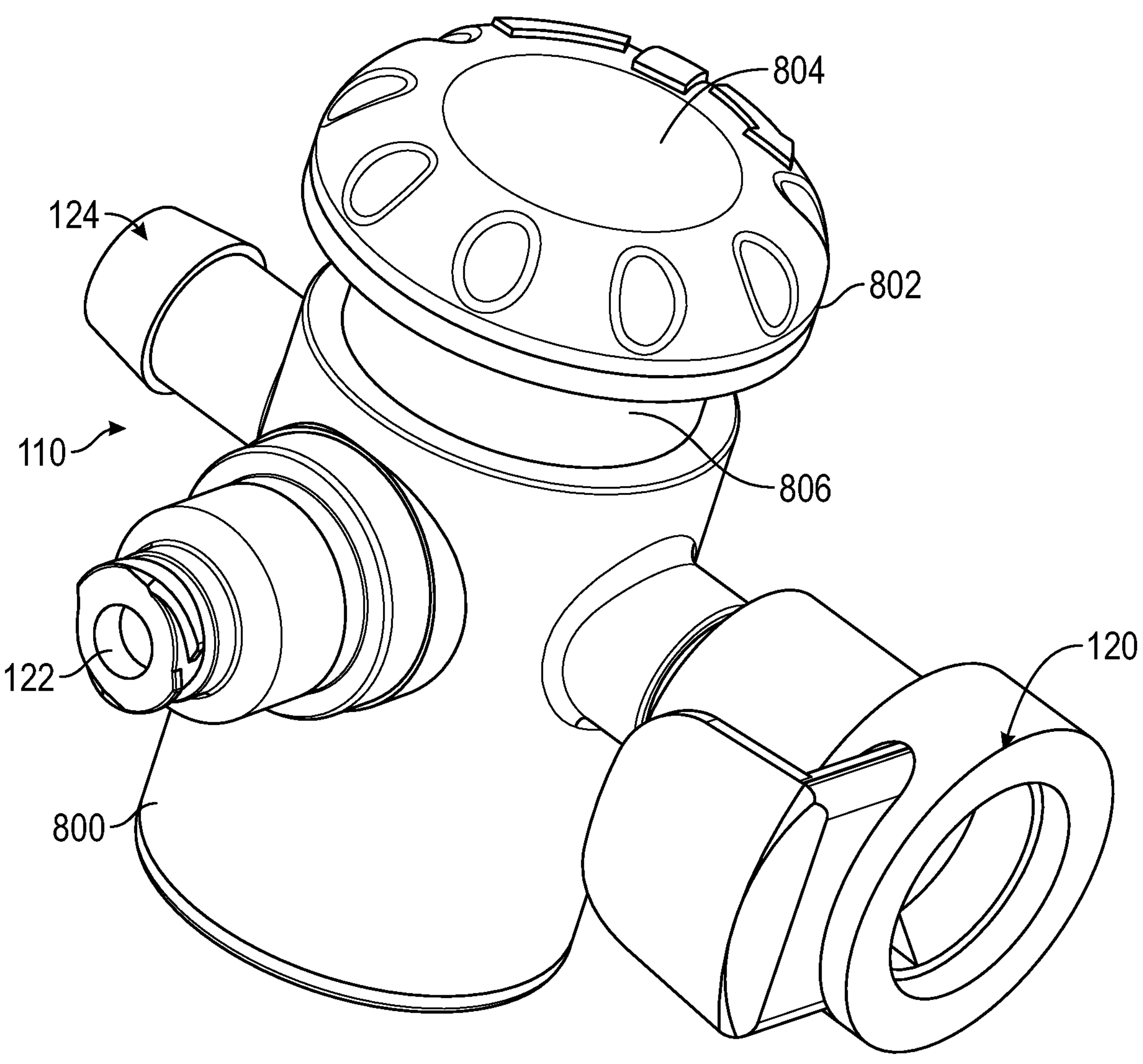
FIG. 8 is a perspective view of one example of an aspiration flush valve.

FIG. 8 is a perspective view of the example aspiration flush valve 110 previously shown in FIG. 1. The aspiration flush valve 110 includes a valve body 800 and a valve operator 802 movably coupled with the valve body 800. As shown in FIG. 8, the valve operator 802 includes a button 804, and the valve operator is actuated in an example with depression of the valve operator 802 by way of the button 804. As described herein, the valve operator 802 in one example includes an operator shaft 806 that includes two or more layers. Actuation of the layered operator shaft 806 selectively toggles the aspiration flush valve 800 between flushing and aspiration configurations.

As further shown in FIG. 8, the aspiration flush valve 110 includes an outlet port 124 configured for communication with the remainder of the thrombectomy system 100 (see FIG. 1) including the delivery catheter 104. The valve 110 further includes a flushing port 122 and an aspiration port 120 to permit one or both of flushing (e.g., including infusion) or aspiration through the thrombectomy system 100 with the valve 110.

Figure 9:
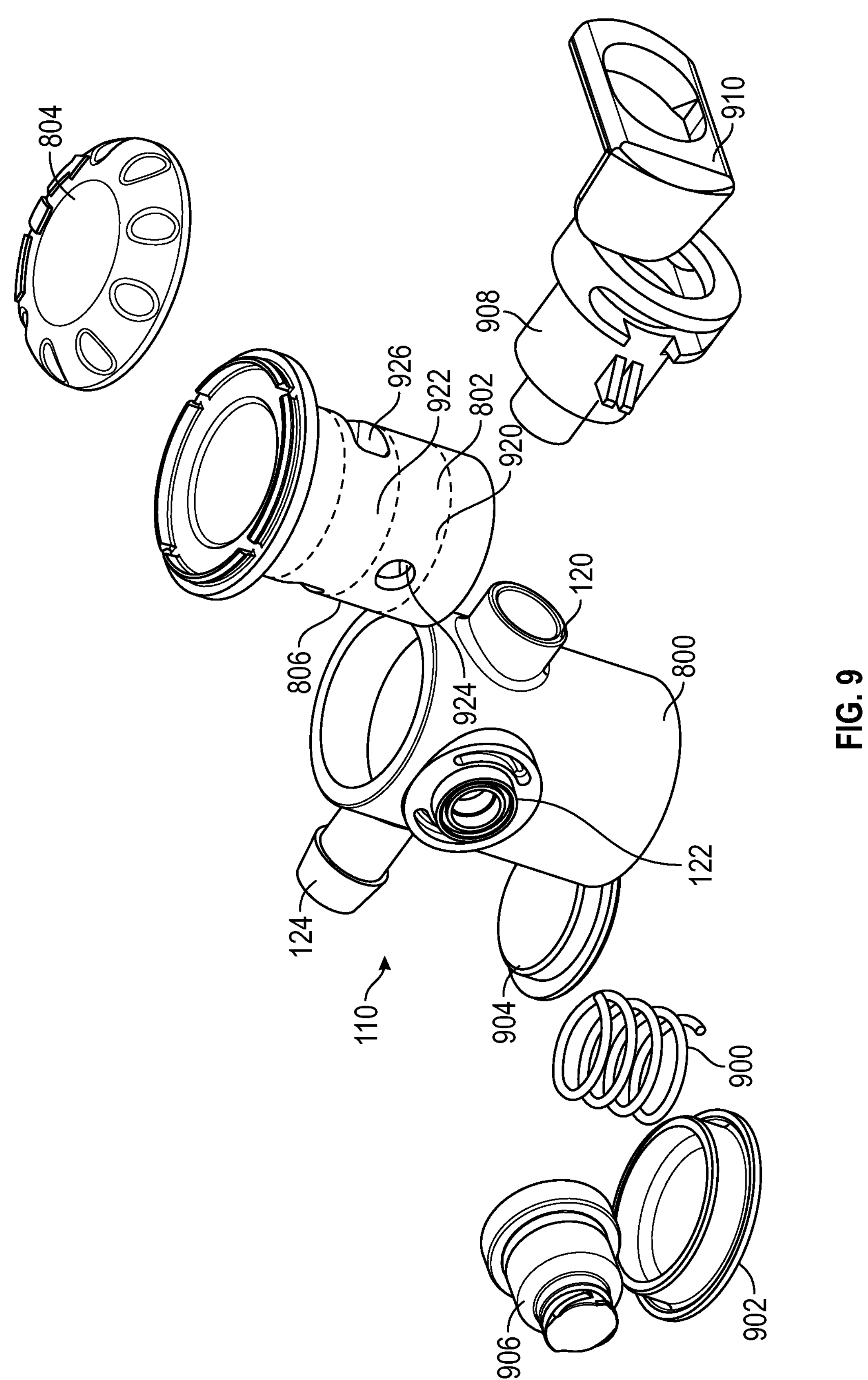
FIG. 9 is an exploded view of the aspiration flush valve of FIG. 8.

FIG. 9 is an exploded view of the aspiration flush valve 110. The valve operator 802 having the operator shaft 806 is shown decoupled from the valve body 800. In this example, the operator shaft 806 includes a flush layer 920 and an aspiration layer 922 separated in this example with broken lines. The flush layer 920 includes a flush lumen 924 that permits communication between the outlet port 124 and the flushing port 122. The aspiration layer 922 includes an aspiration lumen 926 that permits communication between the outlet port and the aspiration port 120. Movement of the valve operator 802 translates the operator shaft 806 within the valve body 800, and accordingly toggles the aspiration flush valve 110 between flushing and aspiration configurations.

Referring again to FIG. 9, the aspiration flush valve 100 further includes a valve biasing element 900. The valve biasing element 900 is, in one example, interposed between a body cap 902 of the valve body 800 and a shaft cap 904 of the valve operator 802. As discussed herein, the valve biasing element 900 biases the valve operator toward the flushing configuration. In one example, the aspiration flush valve 110 closes the aspiration port 120 while in the flushing configuration. As described herein, automatic closing of the aspiration port 120 maintains a negative pressure of the aspiration source 114, such as a vacuum syringe. The aspiration flush valve 110 is operated with the valve operator 802 to selectively interconnect the aspiration port 120 (and aspiration source 114) with the outlet port 124 and the remainder of the thrombectomy system 100. For instance, the clinician operates the valve operator 802 from proximate to the delivery catheter hub 150 to conduct aspiration on as-needed basis.

The aspiration flush valve 110 in this example further includes a flush fitting 906 to permit coupling of a source of flushing fluid including, but not limited to, an infusion reservoir, saline syringe, medicament syringe or the like. In another example, the aspiration flush valve 110 includes an aspiration fitting 908 configured to coupled with an aspiration source, such as the source 114 shown in FIG. 1. As shown in FIG. 1, the aspiration source 114 includes a syringe port 158. In an example, the syringe port 158 includes one or more flanges, recesses, channels or the like configured to cooperatively couple with a fitting detent 910 of the aspiration fitting 908. Optionally, the fitting detent 910 is biased with a biasing element, such as a leaf spring, band or the like. The syringe port 158 overcomes the bias when coupled, and actuation of the fitting detent 910 overcomes the bias when decoupling of the aspiration source 114 is specified. Optionally, one or more of the outlet port 124, aspiration port 120, flushing port 122 or the associated fittings 908, 906 includes gaskets, O-rings, or the like to provide sealed coupling between the features of the thrombectomy system 100 and other related components.

Figure 10A:
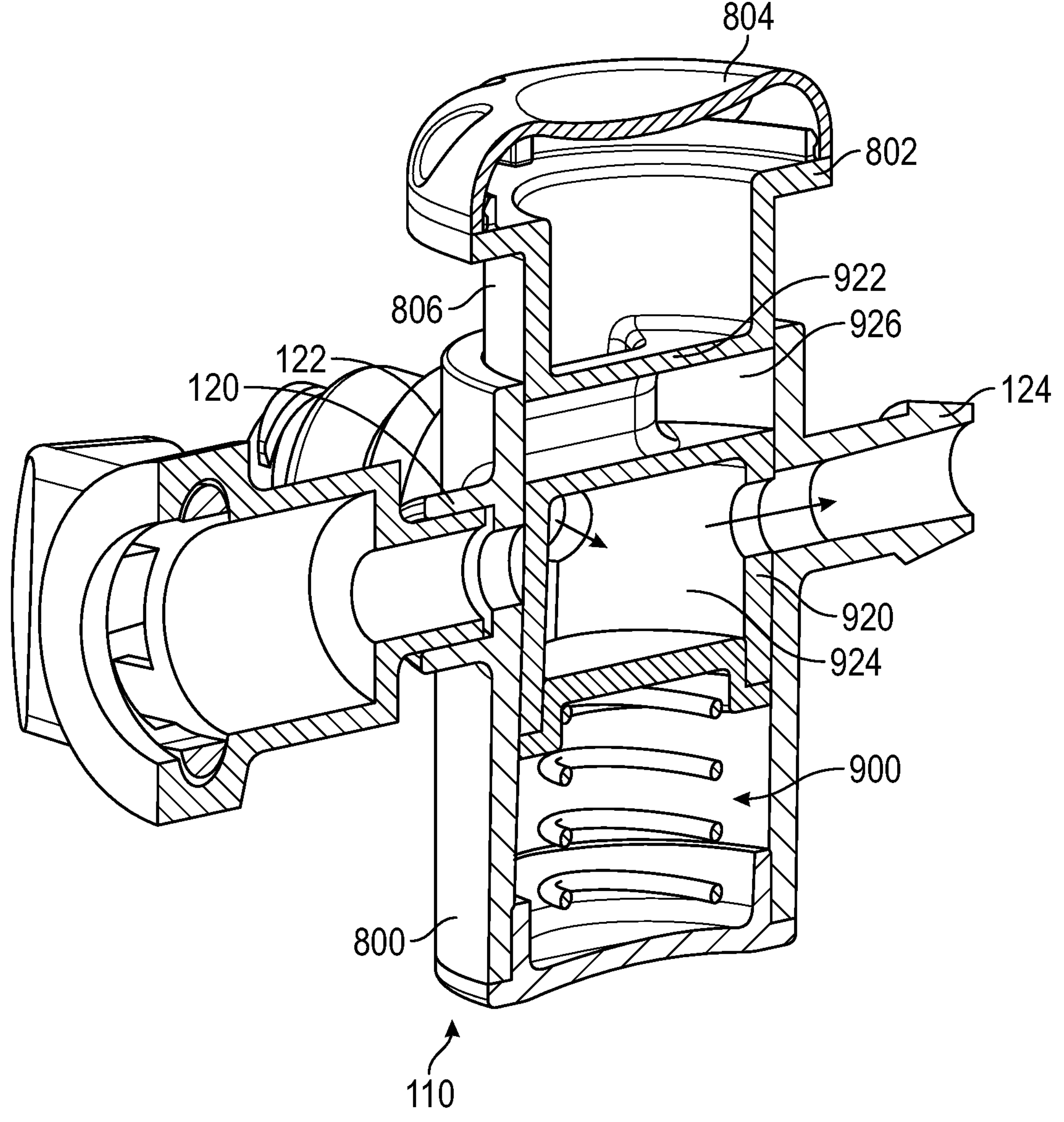
FIG. 10A is a sectional view of the aspiration flush valve in a flushing configuration.

FIG. 10A is a sectional view of the aspiration flush valve 110 in a flushing configuration. In the flushing configuration the valve operator 802, including the operator shaft 806, is raised relative to the position shown in FIG. 10B (the aspiration configuration). In one example, the valve biasing element 900 biases the operator shaft 806 to align the flush layer 920 with the outlet port 124 and the flushing port 122. As shown in the sectional view, the flush layer 920 includes a flush lumen 924, and the flush lumen 924 interconnects the flushing port 122 and the outlet port 124 (see directional arrows). Conversely, the remainder of the flush layer 920, such as portions of the operator shaft 806 positioned at the flush layer 920 block the aspiration port 120, and thereby interrupt communication between the aspiration port 120 (and an aspiration source) and the outlet port 124 along with the remainder of the thrombectomy system 100. In this configuration the clinician may couple a source of flushing fluid with the flushing port and provide the fluid through the aspiration layer 922 of the aspiration flush valve 110 and the outlet port 124 to the thrombectomy system 100.

Figure 10B:
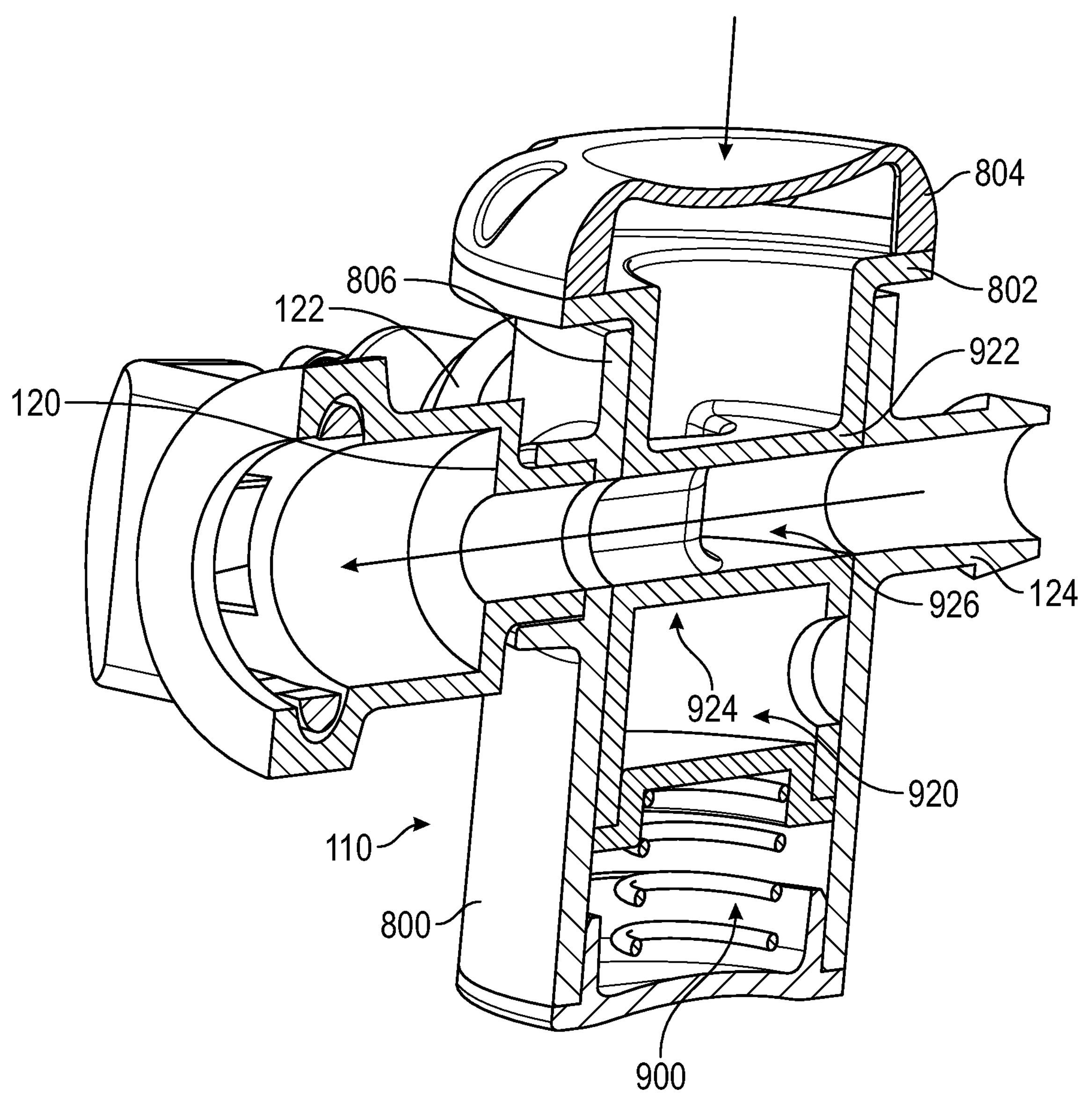
FIG. 10B is a sectional view of the aspiration flush valve in an aspiration configuration.

FIG. 10B illustrates the aspiration flush valve 110 in an aspiration configuration. As shown, the valve operator 802 is moved relative to the flushing configuration (e.g., is depressed with the button 804). The aspiration layer 922 is aligned with the aspiration port 120 and the outlet port 124. The aspiration layer 922 includes an aspiration lumen 926 that extends through the operator shaft 806 and connects the ports 120, 124. Conversely, the flushing port 122 is blocked from the outlet port 124 by the remainder of the aspiration layer 922.

In this configuration the clinician may aspirate the thrombectomy system 100 through the aspiration flush valve 110 while the flush valve is closed by the valve operator 802 and the aspiration layer 922. In one example, an aspiration source 114 is coupled with the aspiration port 120. The clinician operates the valve operator 802 proximate to the delivery catheter hub 150 to overcome the bias of the valve biasing element 900 and align the aspiration layer 922 with the outlet port 124 and the aspiration port 120. When aligned the aspiration source 114 is in communication with the remainder of the thrombectomy system 100, and aspiration is conducted. Relaxing or release of the valve operator 802 permits biasing of the operator 802 toward the flushing configuration and aspiration is arrested. With the thrombectomy system 100 and the aspiration flush valve 110 the clinician readily controls toggling of aspiration for the system, and may do so with the valve 110 proximate to the hub 150 controlling at least some of the thrombectomy functions. The aspiration flush valve 110 provides aspiration in an as-needed fashion. Additionally, by toggling of the valve operator 802 between the flushing and aspiration configurations pressure is varied (e.g., oscillated, pulsed or the like) in the thrombectomy system 100 to assist in freeing clogs or plugs, and moving organized thrombus.

Figure 11:
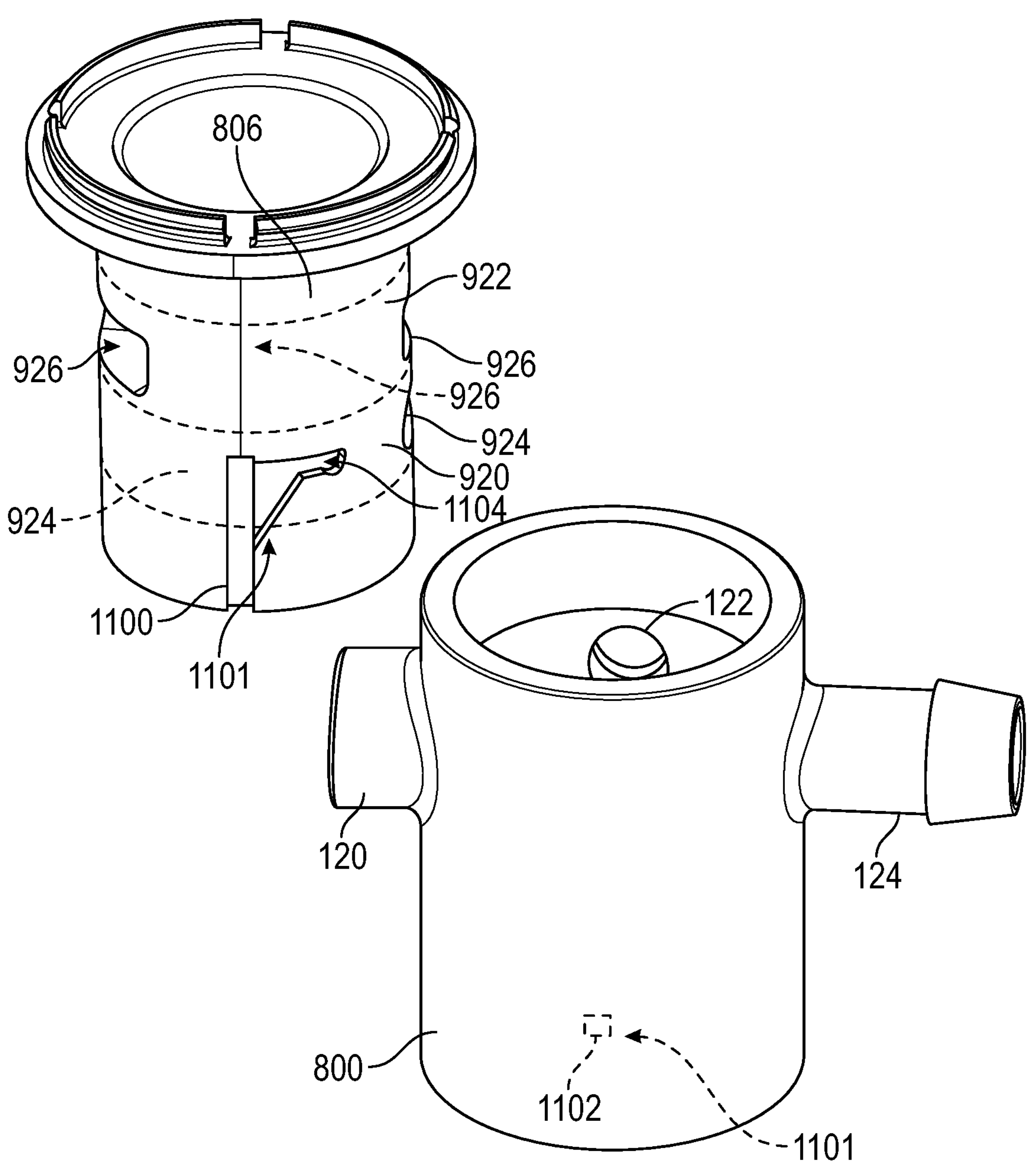
FIG. 11 is another exploded view of a portion of the aspiration flush valve of FIG. 8 including a lock.

In another example, the aspiration flush valve 110 includes a locked aspiration configuration. In this configuration, the valve operator 802 is held in the aspiration configuration, for instance to provide continuous aspiration while freeing the clinician to conduct other tasks or procedures. One example of a lock mechanism 1101 configured to secure the aspiration flush valve 110 in the locked aspiration configuration is shown in FIG. 11. The lock mechanism 1101 includes a bayonet channel 1100 provide on one of the operator shaft 806 or the valve body 800. As shown, the bayonet channel 1100 is provided along the operator shaft 806 and a bayonet flange 1102 is provided with the valve body 800.

The bayonet channel 1100 extends upwardly along the shaft 806 and gradually widens toward a lock securing channel 1104. The bayonet flange 1102 is provided along an opposed surface of the valve body 800 and is configured to slidably move within the bayonet channel 1100. In operation, as the valve operator 802 and the operator shaft 806 are depressed relative to the valve body 800, the bayonet flange relatively travels within the bayonet channel 1100 toward the end having the lock securing channel 1104. In an example, the end of the bayonet channel 1100 arrests further motion of the valve operator 802, and corresponds to the aspiration configuration (e.g., with the aspiration lumen 926 aligned with the outlet port 124 and the aspiration port 120). If securing of the aspiration flush valve 110 in the locked aspiration configuration is specified, the clinician rotates the valve operator 802 and the operator shaft 806 (e.g., clockwise in FIG. 11). Rotation moves the operator shaft 806 and the lock securing channel 1104 into alignment with the bayonet flange 1102 positions the flange at the channel 110 and away from the taper of the bayonet channel 1104. Upon release of the valve operator 802, the operator 802 is biased by the valve biasing element 900 and rests within the lock securing channel 110, thereby holding the valve operator 802 in place with the aspiration lumen 926 in ongoing communication with the aspiration port 120 and the outlet port 124.

In the example of FIG. 11, the lock mechanism 1101 includes a bayonet type fitting. In other examples, the lock mechanism 1101 includes, but is not limited to, a bayonet fitting, detent, interference fit, friction fit, clamp, latch or the like. The lock mechanism 1101 ensures the aspiration flush valve 110 is secured in the locked aspiration configuration, and also provides the clinician the option to conduct selective aspiration for the thrombectomy system 100. For instance, the aspiration flush valve 110 including the lock mechanism is selectively toggled between the flushing and aspiration configurations as well as the locked aspiration configuration.

Various Notes and Aspects

Aspect 1 can include a thrombectomy system comprising: a delivery catheter configured to support one or more thrombectomy instruments, the delivery catheter includes: a delivery catheter hub; and a collection catheter having a collection shaft with a collection lumen (alternatively referred to as delivery catheter having a delivery shaft and a delivery lumen, respectively), the collection shaft is coupled with the delivery catheter hub; and an aspiration flush valve in communication with the collection lumen, the aspiration flush valve includes: an aspiration port; a flushing port; an outlet port in communication with the collection lumen and in selective communication with the aspiration port and the flushing port; and a valve operator movable relative to the aspiration, flushing and outlet ports, the valve operator includes flushing and aspiration configurations: in the flushing configuration the outlet port is in communication with the flushing port; and in the aspiration configuration the outlet port is in communication with the aspiration port.

Aspect 2 can include, or can optionally be combined with the subject matter of Aspect 1, to optionally include wherein the valve operator includes an operator shaft, the operator shaft having: a flush layer including a flush lumen; an aspiration layer including an aspiration lumen; wherein in the flushing configuration the flush lumen interconnects the flushing port and the outlet port; and wherein in the aspiration configuration the aspiration lumen interconnects the aspiration port and the outlet port.

Aspect 3 can include, or can optionally be combined with the subject matter of one or any combination of Aspects 1 or 2 to optionally include wherein translation of the valve operator relative to the valve body is configured to selectively align the flush layer with the flushing port and the outlet port in the flushing configuration and align the aspiration layer with the aspiration port and the outlet port in the aspiration configuration.

Aspect 4 can include, or can optionally be combined with the subject matter of one or any combination of Aspects 1-3 to optionally include wherein the valve operator includes a locked aspiration configuration: in the aspiration configuration the valve operator is biased toward the flushing configuration with the outlet port in communication with the aspiration port; and in the locked aspiration configuration the valve operator is secured with the outlet port in communication with the aspiration port.

Aspect 5 can include, or can optionally be combined with the subject matter of one or any combination of Aspects 1-4 to optionally include a valve biasing element configured to bias the valve operator toward the flushing configuration.

Aspect 6 can include, or can optionally be combined with the subject matter of Aspects 1-5 to optionally include wherein one or more of the valve body or the valve operator includes a lock mechanism configured to selectively maintain the valve operator in the locked aspiration configuration.

Aspect 7 can include, or can optionally be combined with the subject matter of Aspects 1-6 to optionally include wherein the aspiration flush valve is proximate to the delivery catheter hub.

Aspect 8 can include, or can optionally be combined with the subject matter of Aspects 1-7 to optionally include a hemostasis valve coupled with the delivery catheter hub, the hemostasis valve includes: a valve diaphragm configured to seal the collection lumen; a valve defeater having a spanning element movable relative to the valve diaphragm between interconnecting and arrested configurations: in the interconnecting configuration the spanning element having a spanning lumen crosses the valve diaphragm and the spanning lumen extends through the valve diaphragm; and in the arrested configuration the spanning element is retracted from the valve diaphragm.

Aspect 9 can include, or can optionally be combined with the subject matter of Aspects 1-8 to optionally include wherein the valve defeater includes a defeater operator, and the spanning lumen extends through the defeater operator.

Aspect 10 can include, or can optionally be combined with the subject matter of Aspects 1-9 to optionally include wherein in the interconnecting configuration the spanning lumen of the spanning element is aligned with the collection lumen of the collection catheter.

Aspect 11 can include, or can optionally be combined with the subject matter of Aspects 1-10 to optionally include a thrombectomy catheter movably received within the collection lumen of the collection shaft.

Aspect 12 can include, or can optionally be combined with the subject matter of Aspects 1-11 to optionally include wherein the thrombectomy catheter includes: a filter shaft; and one or more collection filters coupled with the filter shaft.

Aspect 13 can include, or can optionally be combined with the subject matter of Aspects 1-12 to optionally include wherein the thrombectomy catheter includes a filter sheath movably coupled over the filter shaft and the one or more collection filters, and the filter sheath is configured to transition the one or more collection filters between compressed and deployed configurations.

Aspect 14 can include, or can optionally be combined with the subject matter of Aspects 1-13 to optionally include wherein the collection shaft of the collection catheter is configured to transition the one or more collection filters between compressed and deployed configurations.

Aspect 15 can include, or can optionally be combined with the subject matter of Aspects 1-14 to optionally include wherein delivery catheter includes: a collection funnel coupled with the collection shaft; and a sheath body movably coupled with the delivery catheter hub, the sheath body configured to selectively cover the collection funnel.

Aspect 16 can include, or can optionally be combined with the subject matter of Aspects 1-15 to optionally include a thrombectomy catheter movably received within the collection lumen of the collection shaft, the thrombectomy catheter configured to extend through the collection funnel.

Aspect 17 can include, or can optionally be combined with the subject matter of Aspects 1-16 to optionally include a hemostasis valve comprising: a valve housing; a valve diaphragm coupled with the valve housing; a valve defeater coupled with the valve housing, the valve defeater includes: a spanning element movably coupled with the valve housing, the spanning element including a spanning lumen; and wherein the valve defeater includes interconnecting and arrested configurations: in the interconnecting configuration the spanning element crosses the valve diaphragm and the spanning lumen extends through the valve diaphragm; and in the arrested configuration the spanning element is withdrawn relative to the interconnecting configuration.

Aspect 18 can include, or can optionally be combined with the subject matter of Aspects 1-17 to optionally include wherein the valve defeater includes a biasing element configured to bias the spanning element toward the arrested configuration.

Aspect 19 can include, or can optionally be combined with the subject matter of Aspects 1-18 to optionally include wherein spanning element includes a tubular element.

Aspect 20 can include, or can optionally be combined with the subject matter of Aspects 1-19 to optionally include wherein the spanning element includes a cage element.

Aspect 21 can include, or can optionally be combined with the subj ect matter of Aspects 1-20 to optionally include wherein the spanning element penetrates the valve diaphragm in the interconnecting configuration.

Aspect 22 can include, or can optionally be combined with the subject matter of Aspects 1-21 to optionally include wherein the spanning lumen is isolated from the valve diaphragm.

Aspect 23 can include, or can optionally be combined with the subject matter of Aspects 1-22 to optionally include a defeater operator movably coupled with the valve housing.

Aspect 24 can include, or can optionally be combined with the subject matter of Aspects 1-23 to optionally include wherein the valve defeater includes the defeater operator, and the spanning lumen extends through the defeater operator.

Aspect 25 can include, or can optionally be combined with the subject matter of Aspects 1-24 to optionally include a delivery catheter configured to support one or more thrombectomy instruments, the delivery catheter includes: a delivery catheter hub coupled with the hemostasis valve; and a collection catheter having a collection shaft with a collection lumen, the collection shaft coupled with the delivery catheter hub.

Aspect 26 can include, or can optionally be combined with the subject matter of Aspects 1-25 to optionally include wherein the hemostasis valve is housed in the delivery catheter hub, and the spanning lumen is aligned with the collection lumen.

Aspect 27 can include, or can optionally be combined with the subject matter of Aspects 1-26 to optionally include wherein the collection shaft is coupled with a collection funnel; and wherein a sheath body is movably coupled with the delivery catheter hub, the sheath body is configured to selectively cover the collection funnel.

Aspect 28 can include, or can optionally be combined with the subject matter of Aspects 1-27 to optionally include an aspiration flush valve comprising: a valve body including: an aspiration port; a flushing port; and an outlet port in selective communication with the aspiration port and the flushing port; a valve operator movably coupled with the valve body, the valve operator includes a flushing configuration, an aspiration configuration, and a locked aspiration configuration: in the flushing configuration the outlet port is in communication with the flushing port; in the aspiration configuration the outlet port is in releasable communication with the aspiration port; and in the locked aspiration configuration the valve operator is secured and the outlet port is in communication with the aspiration port.

Aspect 29 can include, or can optionally be combined with the subject matter of Aspects 1-28 to optionally include wherein the valve operator includes a depressible button.

Aspect 30 can include, or can optionally be combined with the subject matter of Aspects 1-29 to optionally include wherein the depressible button is manually depressed in the aspiration configuration and depressed and locked in the locked aspiration configuration.

Aspect 31 can include, or can optionally be combined with the subject matter of Aspects 1-30 to optionally include wherein one or more of the valve body or the valve operator includes a lock mechanism configured to selectively maintain the valve operator in the locked aspiration configuration.

Aspect 32 can include, or can optionally be combined with the subject matter of Aspects 1-31 to optionally include wherein the lock mechanism includes a bayonet channel in one of the valve operator or the valve body and a bayonet flange in the other of the valve body or the valve operator, and the bayonet flange is received in the bayonet channel in the locked aspiration configuration.

Aspect 33 can include, or can optionally be combined with the subject matter of Aspects 1-32 to optionally include wherein the valve operator includes an operator shaft, the operator shafting having: a flush layer including a flush lumen; an aspiration layer including an aspiration lumen; wherein in the flushing configuration the flush lumen interconnects the flushing port and the outlet port; wherein in the aspiration and the locked aspiration configurations the aspiration lumen interconnects the aspiration port and the outlet port.

Aspect 34 can include, or can optionally be combined with the subject matter of Aspects 1-33 to optionally include wherein translation of the valve operator relative to the valve body is configured to align the flush layer with the flushing port and the outlet port in the flushing configuration and align the aspiration layer with the aspiration port and the outlet port in the aspiration and locked aspiration configurations.

Aspect 35 can include, or can optionally be combined with the subject matter of Aspects 1-34 to optionally include a valve biasing element, and in the aspiration configuration the biasing element biases the valve operator toward the flushing configuration.

Aspect 36 can include, or can optionally be combined with the subject matter of Aspects 1-35 to optionally include wherein in the aspiration configuration ongoing depression of the valve operator overcomes the valve biasing element and maintains the valve operator in the aspiration configuration.

Aspect 37 can include, or can optionally be combined with the subject matter of Aspects 1-36 to optionally include a delivery catheter configured to support one or more thrombectomy instruments, the delivery catheter includes: a delivery catheter hub coupled with the aspiration flush valve; and a collection catheter having a collection shaft with a collection lumen, the collection shaft coupled with the delivery catheter hub.

Aspect 38 can include, or can optionally be combined with the subject matter of Aspects 1-37 to optionally include wherein the aspiration flush valve is proximate to the delivery catheter hub and in communication with the collection lumen.

Aspect 39 can include, or can optionally be combined with the subject matter of Aspects 1-38 to optionally include wherein the collection shaft is coupled with a collection funnel; and wherein a sheath body is movably coupled with the delivery catheter hub, the sheath body is configured to selectively cover the collection funnel.

Each of these non-limiting aspects can stand on its own, or can be combined in various permutations or combinations with one or more of the other aspects.

The above description includes references to the accompanying drawings, which form a part of the detailed description. The drawings show, by way of illustration, specific embodiments in which the invention can be practiced. These embodiments are also referred to herein as "aspects" or "examples." Such aspects or example can include elements in addition to those shown or described. However, the present inventors also contemplate aspects or examples in which only those elements shown or described are provided. Moreover, the present inventors also contemplate aspects or examples using any combination or permutation of those elements shown or described (or one or more features thereof), either with respect to a particular aspects or examples (or one or more features thereof), or with respect to other Aspects (or one or more features thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

The above description is intended to be illustrative, and not restrictive. For example, the above-described aspects or examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as aspects, examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A thrombectomy system comprising:

a delivery catheter configured to support one or more thrombectomy instruments, the delivery catheter includes:
  - a delivery catheter hub; and
  - a collection catheter having a collection shaft with a collection lumen, the collection shaft is coupled with the delivery catheter hub;
  - an aspiration flush valve in communication with the collection lumen, the aspiration flush valve includes:
    - an aspiration port;
    - a flushing port;
    - an outlet port in communication with the collection lumen and in selective communication with the aspiration port and the flushing port; and
    - a valve operator movable relative to the aspiration, flushing and outlet ports, the valve operator includes flushing and aspiration configurations:
      - in the flushing configuration the outlet port is in communication with the flushing port; and
      - in the aspiration configuration the outlet port is in communication with the aspiration port through a valve operator aspiration lumen separate from the flushing lumen; and
  - wherein the delivery catheter hub includes a hemostasis valve, the hemostasis valve includes:
    - a valve diaphragm configured to seal the collection lumen;
    - a valve defeater having a spanning element movable relative to the valve diaphragm between interconnecting and arrested configurations:
      - in the interconnecting configuration the spanning element having a spanning lumen crosses the valve diaphragm and the spanning lumen extends through the valve diaphragm; and
      - in the arrested configuration the spanning element is retracted from the valve diaphragm.

2. The thrombectomy system of claim 1, wherein the valve operator includes an operator shaft, the operator shaft having:
a flush layer including a flush lumen;
an aspiration layer including an aspiration lumen, the flush and aspiration lumens are separate;
wherein in the flushing configuration the flush lumen interconnects the flushing port and the outlet port; and
wherein in the aspiration configuration the aspiration lumen interconnects the aspiration port and the outlet port.

3. The thrombectomy system of claim 2, wherein translation of the valve operator relative to the valve body is configured to selectively align the flush layer with the flushing port and the outlet port in the flushing configuration and align the aspiration layer with the aspiration port and the outlet port in the aspiration configuration.

4. The thrombectomy system of claim 2, wherein the valve operator includes a locked aspiration configuration:
in the aspiration configuration the valve operator is biased toward the flushing configuration with the outlet port in communication with the aspiration port; and
in the locked aspiration configuration the valve operator is secured with the outlet port in communication with the aspiration port.

5. The thrombectomy system of claim 4 comprising a valve biasing element configured to bias the valve operator toward the flushing configuration.

6. The thrombectomy system of claim 4, wherein one or more of the valve body or the valve operator includes a lock mechanism configured to selectively maintain the valve operator in the locked aspiration configuration.

7. The thrombectomy system of claim 1, wherein the aspiration flush valve is proximate to the delivery catheter hub.

8. The thrombectomy system of claim 1 comprising a thrombectomy catheter movably received within the collection lumen of the collection shaft.

9. The thrombectomy system of claim 8, wherein the thrombectomy catheter includes:
a filter shaft; and
one or more collection filters coupled with the filter shaft.

10. The thrombectomy system of claim 9, wherein the thrombectomy catheter includes a filter sheath movably coupled over the filter shaft and the one or more collection filters, and the filter sheath is configured to transition the one or more collection filters between compressed and deployed configurations.

11. The thrombectomy system of claim 9, wherein the collection shaft of the collection catheter is configured to transition the one or more collection filters between compressed and deployed configurations.

12. The thrombectomy system of claim 11 comprising the thrombectomy catheter movably received within the collection lumen of the collection shaft, the thrombectomy catheter configured to extend through the collection funnel.

13. The thrombectomy system of claim 1, wherein delivery catheter includes:
a collection funnel coupled with the collection shaft; and
a sheath body movably coupled with the delivery catheter hub, the sheath body configured to selectively cover the collection funnel.

14. The thrombectomy system of claim 1, wherein the hemostasis valve includes a biasing element coupled with the valve defeater, and the biasing element is configured to bias the valve defeater toward the arrested configuration.

15. The thrombectomy system of claim 1, wherein upon release the valve defeater the valve defeater is biased toward the arrested configuration and the valve diaphragm closes around an instrument spanning the valve diaphragm.

16. The thrombectomy system of claim 1, wherein in the interconnecting configuration the spanning element having the spanning lumen provides a continuous interface between collection lumen and the spanning lumen.

17. The thrombectomy system of claim 1, wherein the valve defeater includes a defeater operator, the spanning lumen extends through the defeater operator, and the valve defeater includes a depressible button biased toward the arrested configuration.

18. The thrombectomy system of claim 1, wherein in the interconnecting configuration the spanning lumen of the spanning element is aligned with the collection lumen of the collection catheter.

19. An aspiration flush valve comprising:
a valve body including:
an aspiration port;
a flushing port; and
an outlet port in selective communication with the aspiration port and the flushing port;
a valve operator movably coupled with the valve body, the valve operator includes a flushing configuration and an aspiration configuration:
in the flushing configuration the outlet port is in communication with the flushing port through a valve operator flushing lumen; and
in the aspiration configuration the outlet port is in releasable communication with the aspiration port through a valve operator aspiration lumen separate from the flushing lumen.

20. The aspiration flush valve of claim 19, wherein the valve operator includes a depressible button.

21. The aspiration flush valve of claim 20, wherein the depressible button is manually depressed in the aspiration configuration and depressed and locked in the locked aspiration configuration.

22. The aspiration flush valve of claim 19, wherein one or more of the valve body or the valve operator includes a lock mechanism configured to selectively maintain the valve operator in the locked aspiration configuration.

23. The aspiration flush valve of claim 22, wherein the lock mechanism includes a bayonet channel in one of the valve operator or the valve body and a bayonet flange in the other of the valve body or the valve operator, and the bayonet flange is received in the bayonet channel in the locked aspiration configuration.

24. The aspiration flush valve of claim 19, wherein the valve operator includes an operator shaft, the operator shafting having:
a flush layer including a flush lumen;
an aspiration layer including an aspiration lumen;
wherein in the flushing configuration the flush lumen interconnects the flushing port and the outlet port;
wherein in the aspiration and the locked aspiration configurations the aspiration lumen interconnects the aspiration port and the outlet port.

25. The aspiration flush valve of claim 24, wherein translation of the valve operator relative to the valve body is configured to align the flush layer with the flushing port and the outlet port in the flushing configuration and align the aspiration layer with the aspiration port and the outlet port in the aspiration and locked aspiration configurations.

26. The aspiration flush valve of claim 19 comprising a valve biasing element, and in the aspiration configuration the biasing element biases the valve operator toward the flushing configuration.

27. The aspiration flush valve of claim 26, wherein in the aspiration configuration ongoing depression of the valve operator overcomes the valve biasing element and maintains the valve operator in the aspiration configuration.

28. The aspiration flush valve of claim 19 comprising a delivery catheter configured to support one or more thrombectomy instruments, the delivery catheter includes:

a delivery catheter hub coupled with the aspiration flush valve; and a collection catheter having a collection shaft with a collection lumen, the collection shaft coupled with the delivery catheter hub.

29. The aspiration flush valve of claim 28, wherein the aspiration flush valve is proximate to the delivery catheter hub and in communication with the collection lumen.

30. The aspiration flush valve of claim 28, wherein the collection shaft is coupled with a collection funnel; and wherein a sheath body is movably coupled with the delivery catheter hub, the sheath body is configured to selectively cover the collection funnel.

31. The aspiration flush valve of claim 19, wherein the valve operator includes a locked aspiration configuration:

in the locked aspiration configuration the valve operator is secured and the outlet port is in communication with the aspiration port.

* * * * *